(12) United States Patent
Fischer et al.

(10) Patent No.: US 7,994,364 B2
(45) Date of Patent: Aug. 9, 2011

(54) CRYSTALLINE FORMS OF (−)-(1R,2R)-3-(3-DIMETHYLAMINO-1-ETHYL-2-METHYLPROPYL)-PHENOL HYDROCHLORIDE

(75) Inventors: Andreas Fischer, Huertgenwald (DE); Helmut Buschmann, Esplugues de Llobregat (ES); Michael Gruss, Aachen (DE); Dagmar Lischke, Eschweiler (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 12/634,777

(22) Filed: Dec. 10, 2009

(65) Prior Publication Data

US 2010/0160447 A1     Jun. 24, 2010

Related U.S. Application Data

(63) Continuation of application No. 12/274,747, filed on Nov. 20, 2008, now abandoned, which is a continuation of application No. 11/646,232, filed on Dec. 28, 2006, now abandoned, which is a continuation of application No. PCT/EP2005/006884, filed on Jun. 27, 2005.

(30) Foreign Application Priority Data

Jun. 28, 2004  (EP) .................... 04015091

(51) Int. Cl.
*C07C 211/00* (2006.01)
*A01N 33/02* (2006.01)
*A61K 31/135* (2006.01)

(52) U.S. Cl. ....................... 564/336; 514/649

(58) Field of Classification Search .............. None
See application file for complete search history.

(56) References Cited

U.S. PATENT DOCUMENTS

| | | |
|---|---|---|
| 6,248,737 B1 | 6/2001 | Buschmann et al. |
| 6,344,558 B1 | 2/2002 | Buschmann et al. |
| 2005/0058706 A1 | 3/2005 | Bartholomaeus et al. |
| 2005/0176790 A1 | 8/2005 | Bartholomaus et al. |

FOREIGN PATENT DOCUMENTS

| | | |
|---|---|---|
| EP | 0 693 475 | 1/1996 |
| WO | WO 03/035053 | 5/2003 |

OTHER PUBLICATIONS

International Preliminary Report on Patentability dated Dec. 28, 2006, and PCT/ISA/237 (Written Opinion of the International Searching Authority) (seven (7) pages).

Remington: The Science and Practice of Pharmacy, Nineteenth Edition, vol. 1, pp. 156-168, 180, 1448-1460 (English counterpart of A.R. Gennaro, Remington Farmacia, 19th Ed. Medica Panamericana 1995, pp. 230-235, 245 and 2226-2234 cited against corresponding.

*Primary Examiner* — Daniel Sullivan
*Assistant Examiner* — Clinton Brooks
(74) *Attorney, Agent, or Firm* — Crowell & Moring LLP

(57) ABSTRACT

A hitherto unknown crystalline form of (−)-(1R,2R)-3-(3-dimethylamino-1-ethyl-2-methylpropyl)-phenol hydrochloride, pharmaceutical compositions containing the new crystalline form, methods of producing the new crystalline form, and a related method of use including treatment of, e.g., pain and/or urinary incontinence.

27 Claims, 8 Drawing Sheets

XRPD pattern of Form A

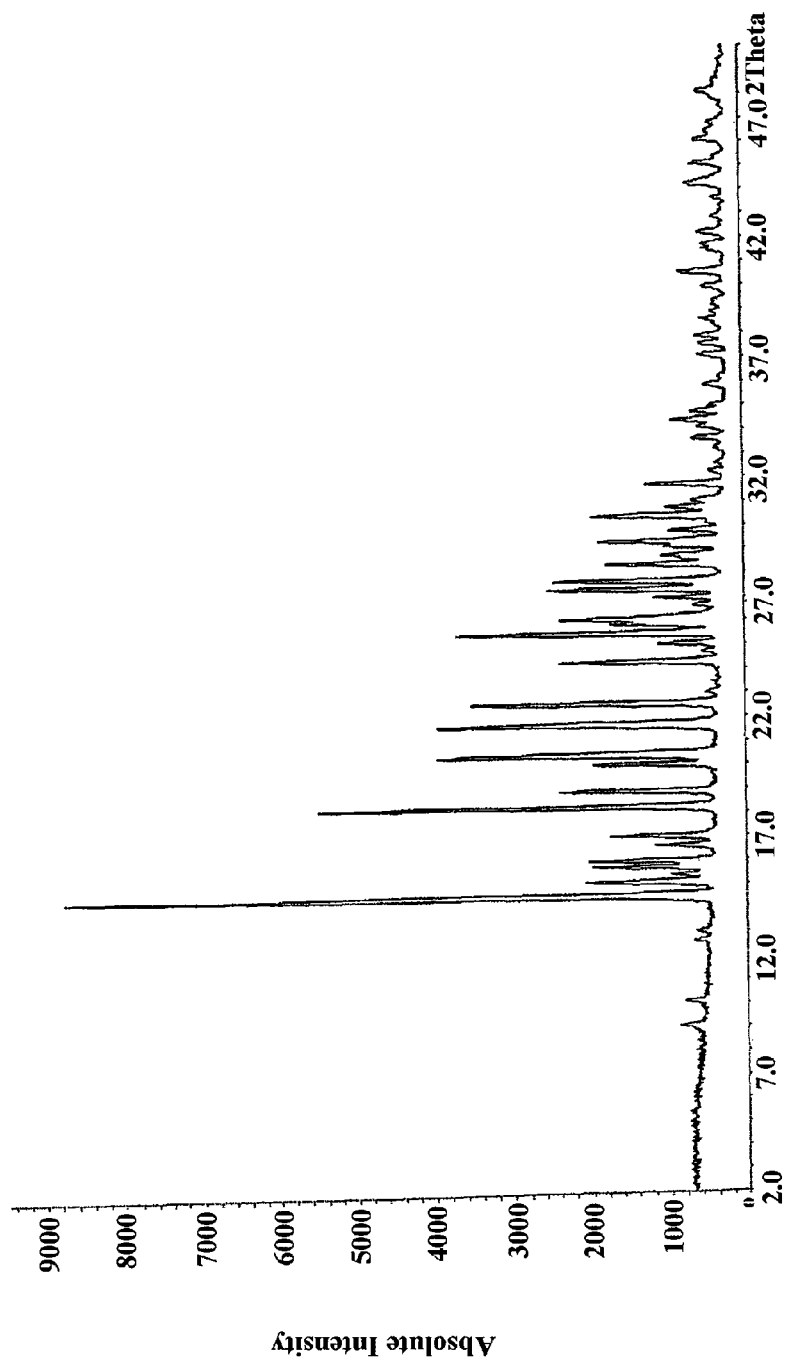
Fig. 1: XRPD pattern of Form A

Fig.2: Infrared spectrum of Form A
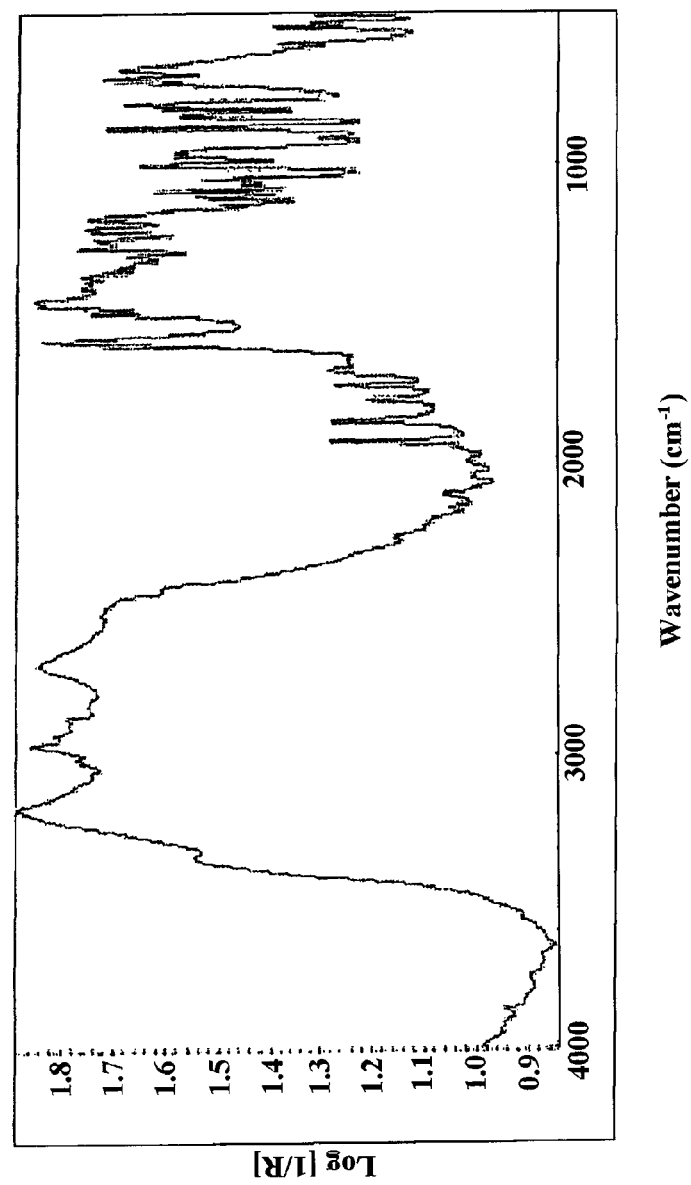

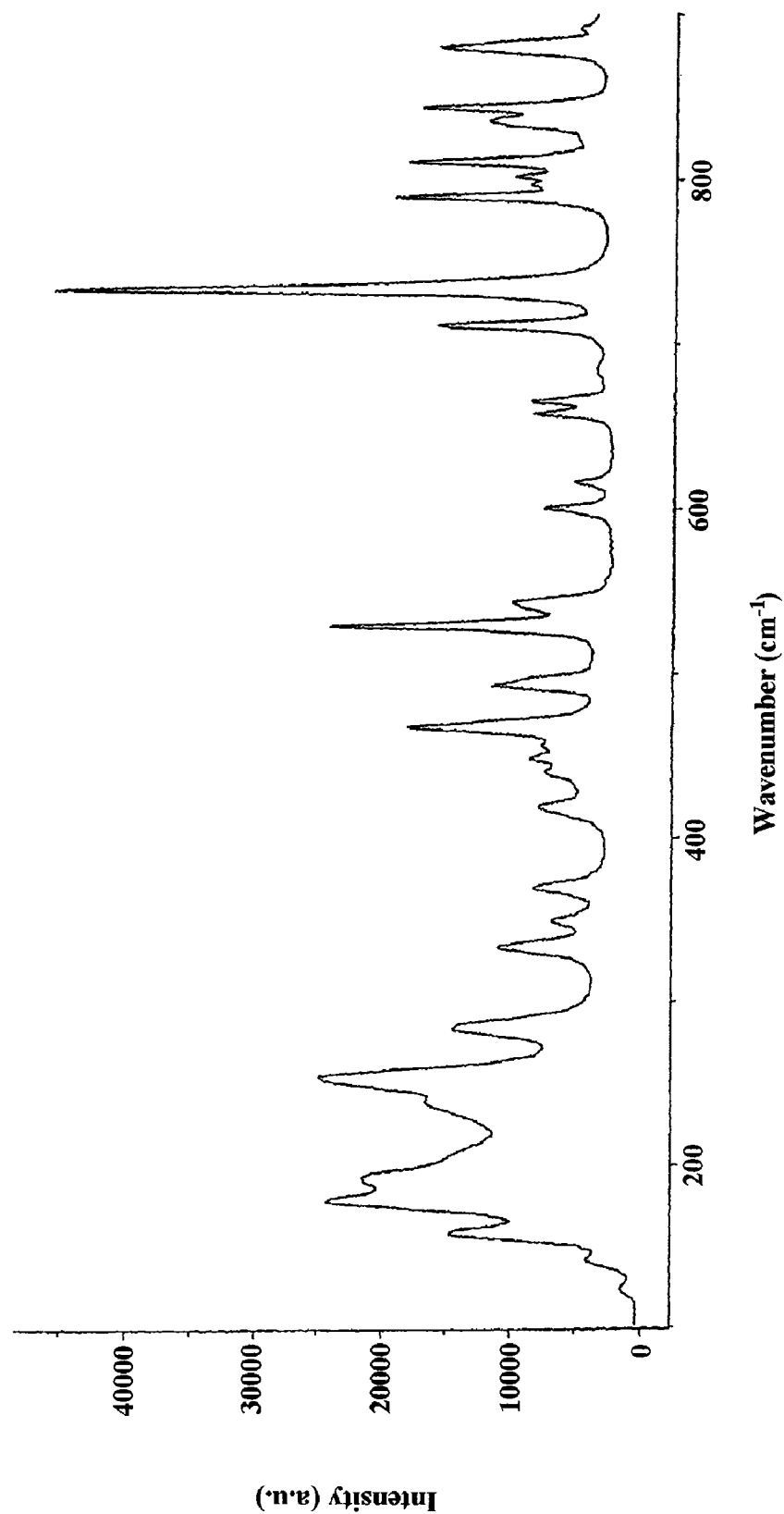

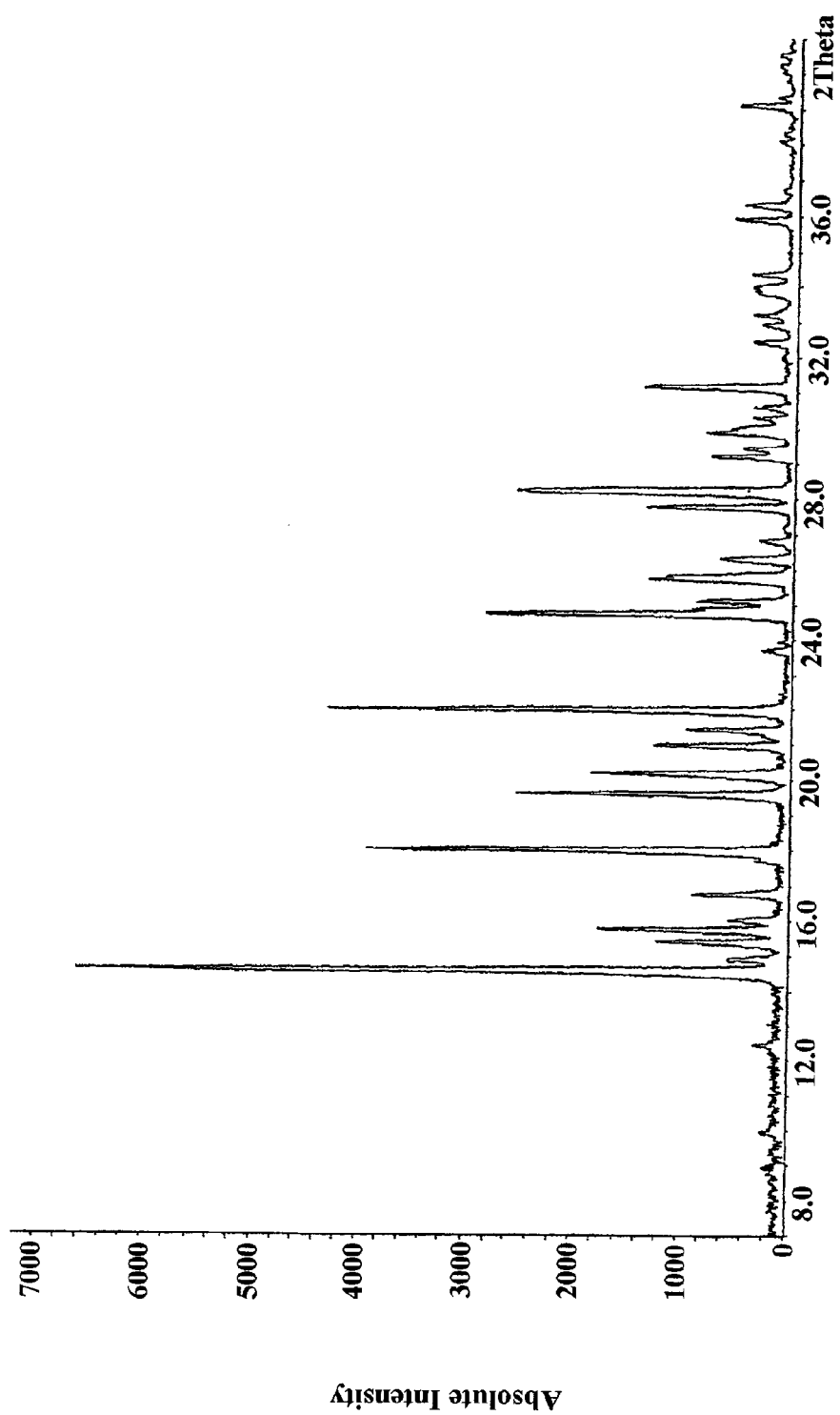
Fig. 4: XRPD pattern of Form B

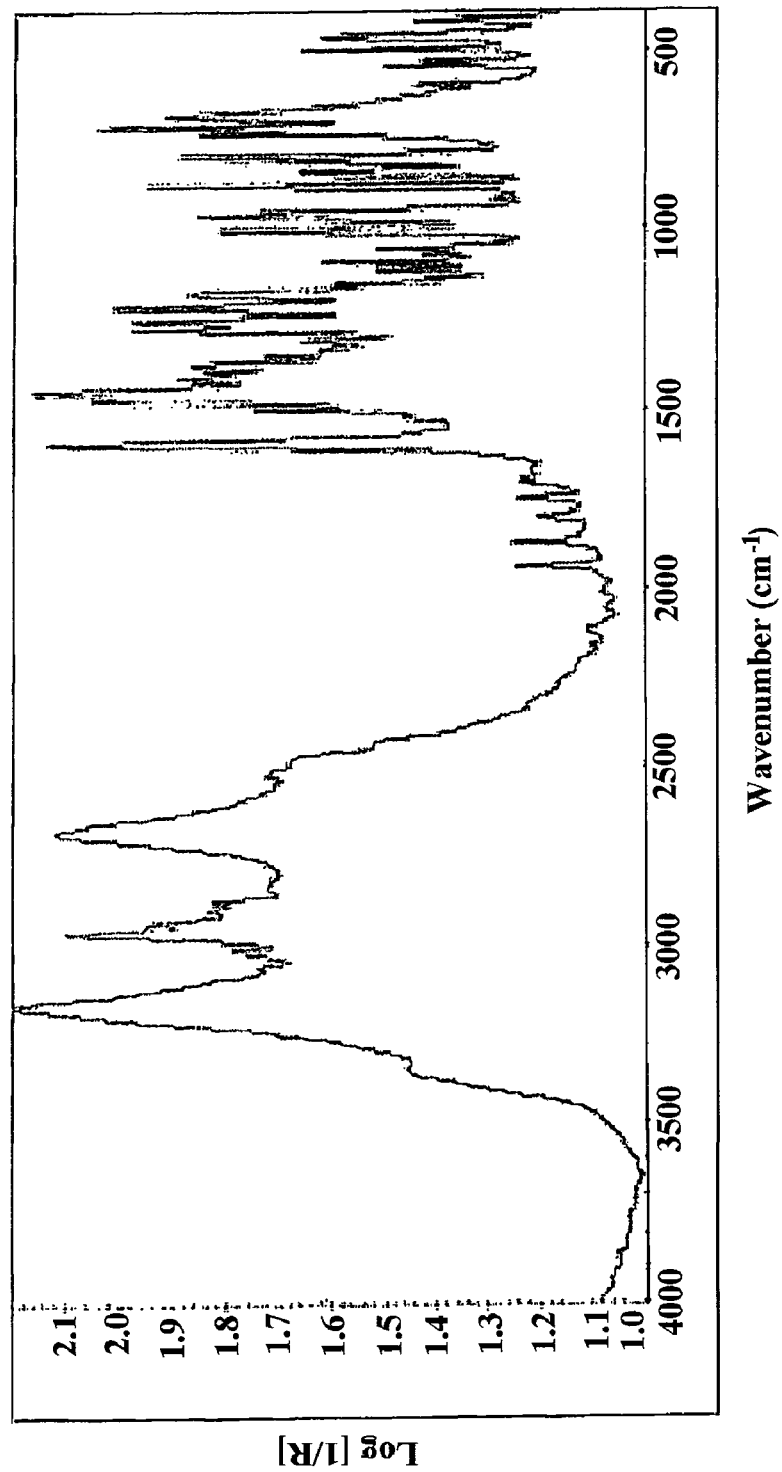
Fig. 5: Infrared spectrum of Form B

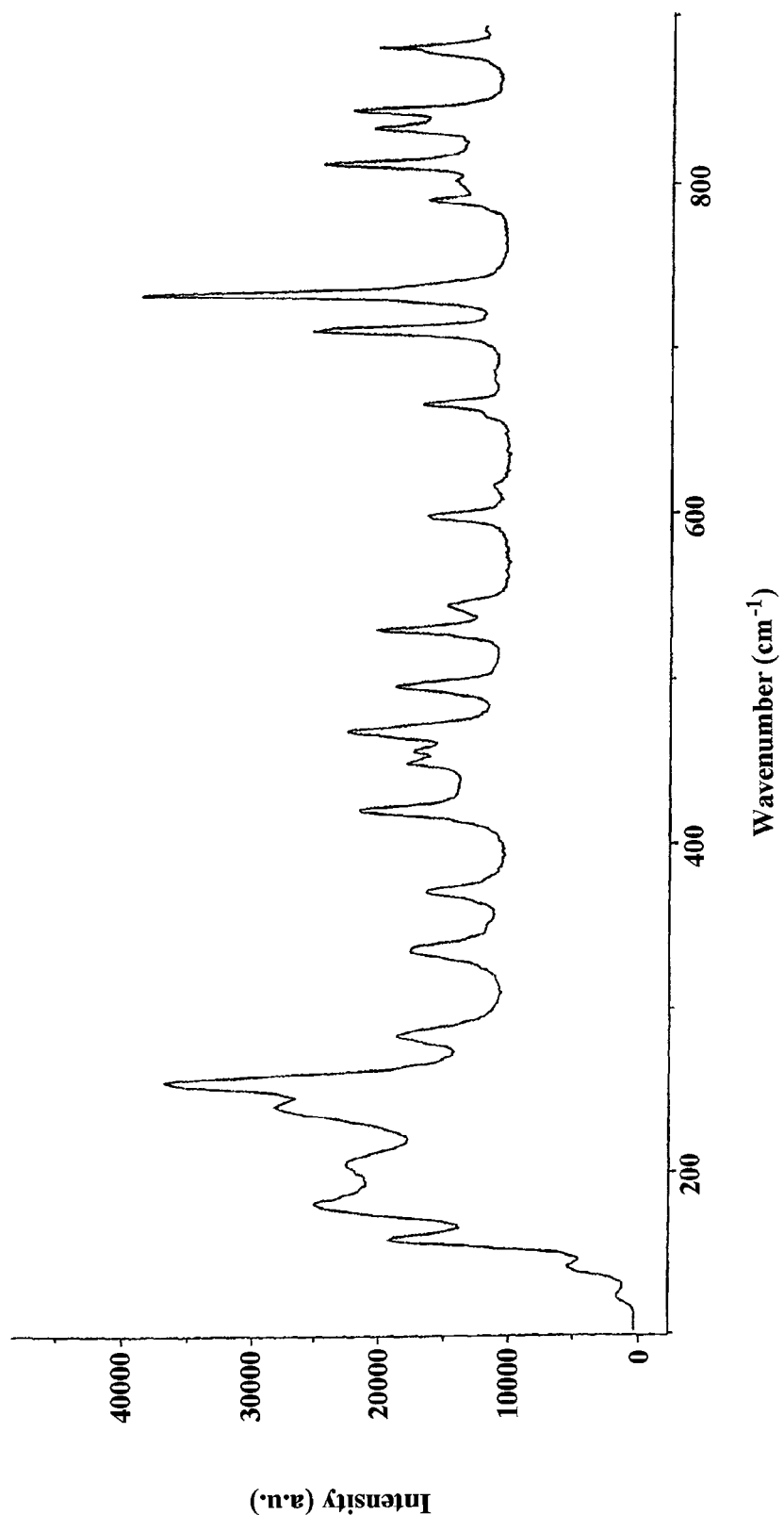

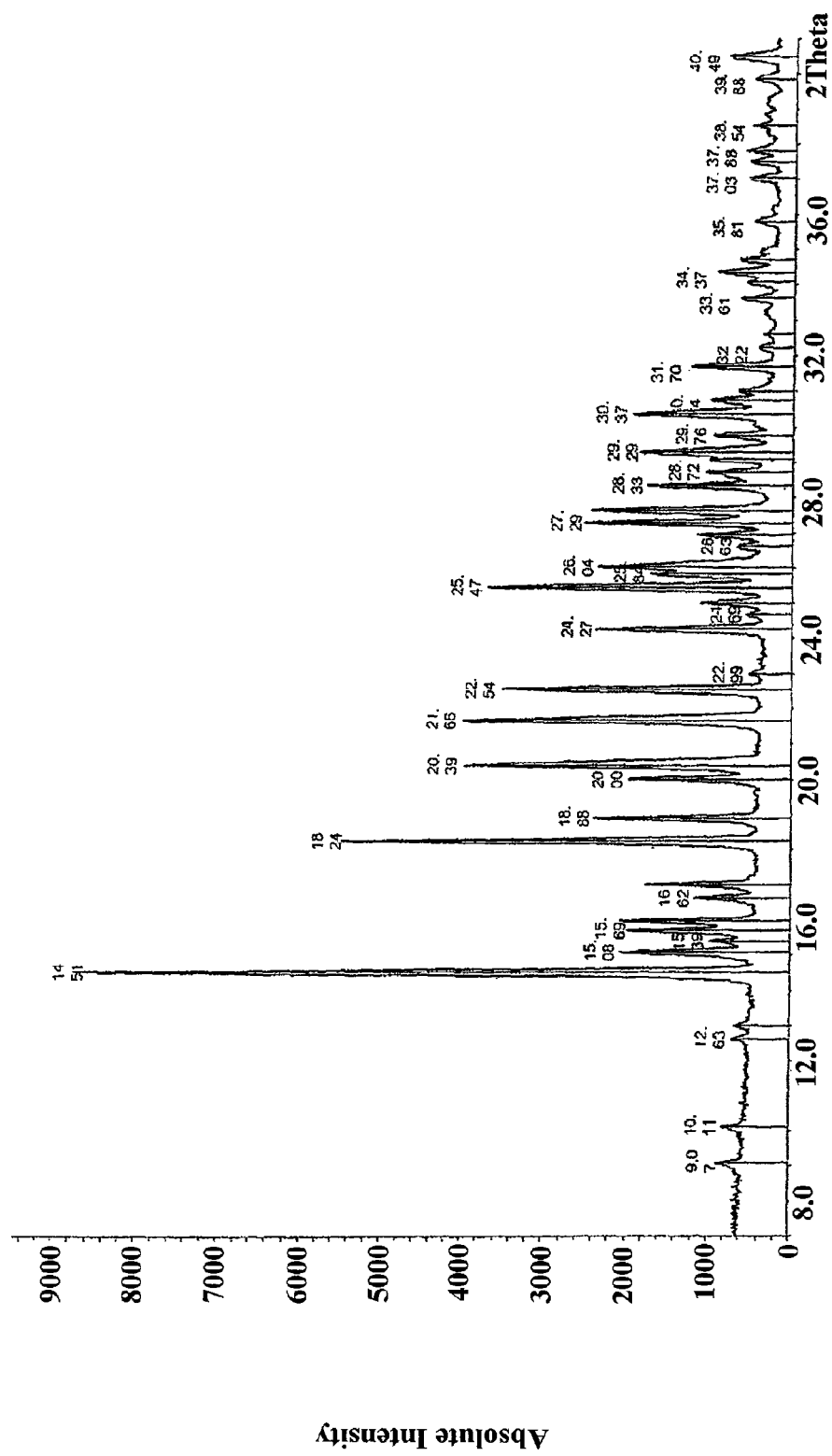
Fig. 7: labelled XRPD pattern of Form A

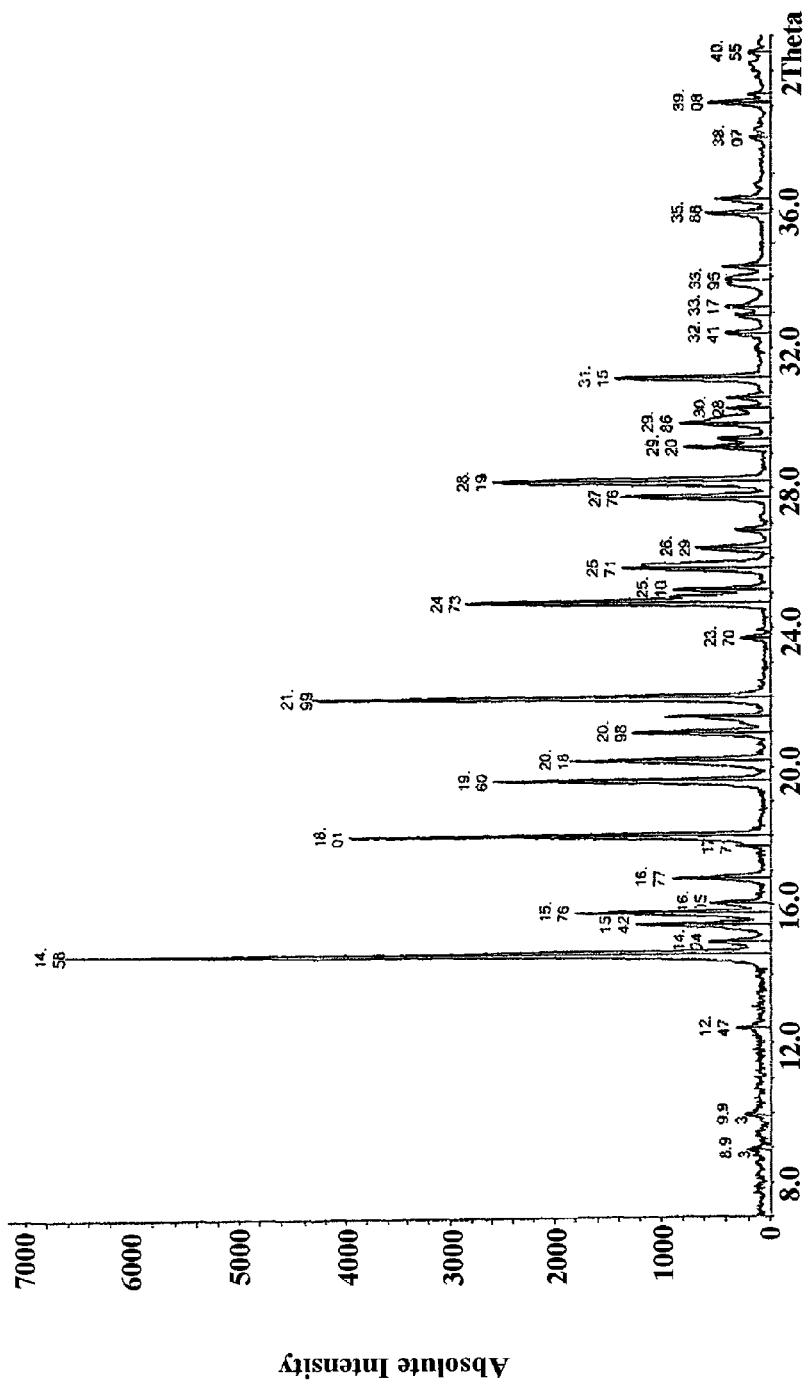

CRYSTALLINE FORMS OF (−)-(1R,2R)-3-(3-DIMETHYLAMINO-1-ETHYL-2-METHYLPROPYL)-PHENOL HYDROCHLORIDE

CROSS-REFERENCE TO RELATED APPLICATIONS

This application is a continuation of co-pending application Ser. No. 12/274,747, filed Nov. 20, 2008, which in turn was a continuation of application Ser. No. 11/646,232, filed Dec. 28, 2006, now abandoned, which in turn was a continuation of International patent application no. PCT/EP2005/006884, filed Jun. 27, 2005, which claims benefit of European patent application Serial No. 04015091.4 filed Jun. 28, 2004, the entire disclosures of which are hereby incorporated in their entirety.

FIELD OF THE INVENTION

This invention relates to solid crystalline forms of (−)-(1R,2R)-3-(3-dimethylamino-1-ethyl-2-methylpropyl)-phenol hydrochloride compounds, methods of producing these compounds, and related treatments, including use as analgesics as well as pharmaceutical compositions containing these compounds.

BACKGROUND OF THE INVENTION

The treatment of pain conditions is of great importance in medicine. There is currently a world-wide need for additional pain therapy. The pressing requirement for a target-oriented treatment of pain conditions which is right for the patient, which is to be understood as the successful and satisfactory treatment of pain for the patients, is documented in the large number of scientific works which have recently and over the years appeared in the field of applied analgesics or on basic research on nociception.

BRIEF SUMMARY OF THE INVENTION

One object of the present invention is to provide new solid forms of (−)-(1R,2R)-3-(3-dimethylamino-1-ethyl-2-methylpropyl)-phenol hydrochloride useful in the treatment or inhibition of pain.

U.S. Pat. Nos. 6,248,737 and 6,344,558 as well as European Patent EP 693 475 B1 disclose the substance and the synthesis of (−)-(1R,2R)-3-(3-dimethylamino-1-ethyl-2-methylpropyl)-phenol hydrochloride in example 25. As proven by X-ray diffraction the 1R,2R configuration as shown in the drawing of the structure in example 25 is correct although the configuration is reported as (−)-(1R,2S) in U.S. Pat. No. 6,248,737 and (−)-(1S,2S) in U.S. Pat. No. 6,344,558 as well as in EP 693 475 B1.

It has now been surprisingly found that (−)-(1R,2R)-3-(3-dimethylamino-1-ethyl-2-methylpropyl)-phenol hydrochloride can be produced in a reproducible manner in two different crystalline forms. The present invention provides a new form (Form A) of (−)-(1R,2R)-3-(3-dimethylamino-1-ethyl-2-methylpropyl)-phenol hydrochloride which is different from the form already known (Form B) obtained by the procedure described in example 25 of U.S. Pat. No. 6,248,737 and U.S. Pat. No. 6,344,558 as well as EP 693 475 B1. This new Form A of (−)-(1R,2R)-3-(3-dimethylamino-1-ethyl-2-methylpropyl)-phenol hydrochloride is very stable at ambient conditions and therefore useful for producing a pharmaceutical composition.

BRIEF DESCRIPTION OF THE DRAWINGS

FIG. 1 shows an X-ray diffraction pattern;
FIG. 2 shows an infrared spectrum;
FIG. 3 shows a RAMAN spectrum;
FIG. 4 shows an X-ray diffraction pattern;
FIG. 5 shows an infrared spectrum;
FIG. 6 shows a RAMAN spectrum;
FIG. 7 shows an X-ray diffraction pattern;
FIG. 8 shows an X-ray diffraction pattern

SUMMARY OF THE INVENTION

The new crystalline Form A of (−)-(1R,2R)-3-(3-dimethylamino-1-ethyl-2-methylpropyl)-phenol hydrochloride can be identified by X-ray powder diffraction. The X-ray diffraction ("XRPD") pattern is shown in FIG. 1 with the peak listing shown as Table 1.

The most important X-ray lines (2-theta values) in terms of intensity characterizing Form A of (−)-(1R,2R)-3-(3-dimethylamino-1-ethyl-2-methylpropyl)-phenol hydrochloride showing one or a combination of the following in a powder diffraction measurement when measured using Cu $K_\alpha$ radiation at ambient temperature are 14.5±0.2, 18.2±0.2, 20.4±0.2, 21.7±0.2 and 25.5±0.2.

To discriminate crystalline Form A of (−)-(1R,2R)-3-(3-dimethylamino-1-ethyl-2-methylpropyl)-phenol hydrochloride from Form B it is more advantageous to look at the unique peaks in the X-ray diffraction diagram, i.e. e.g. the lines with sufficient intensity at 2-theta values, where Form B does not show lines with significant intensity. Such characteristic X-ray lines (2-theta values) for Form A in a powder diffraction pattern when measured using $CuK_\alpha$ radiation at ambient temperature are: 15.1±0.2, 16.0±0.2, 18.9±0.2, 20.4±0.2, 22.5±0.2, 27.3±0.2, 29.3±0.2 and 30.4±0.2.

Another method to identify crystalline Form A of (−)-(1R,2R)-3-(3-dimethylamino-1-ethyl-2-methylpropyl)-phenol hydrochloride is IR-spectroscopy. The IR-Spectrum of Form A is shown as FIG. 2 with the peak listing shown in comparison to Form B as Table 2.

In the IR-spectrum it is characteristic for crystalline Form A of (−)-(1R,2R)-3-(3-dimethylamino-1-ethyl-2-methylpropyl)-phenol hydrochloride to show a combination of the following IR bands: 3180±4 $cm^{-1}$, 2970±4 $cm^{-1}$, 2695±4 $cm^{-1}$, 2115±4 $cm^{-1}$, 1698±4 $cm^{-1}$, 1462±4 $cm^{-1}$, 1032±4 $cm^{-1}$ and/or 972±4 $cm^{-1}$.

RAMAN technique can also be used to identify of the crystalline Form A of (−)-(1R,2R)-3-(3-dimethylamino-1-ethyl-2-methylpropyl)-phenol hydrochloride. Especially the range between 800 $cm^{-1}$ and 200 $cm^{-1}$, which is shown in FIG. 3, is advantageously used also by way of RAMAN microscopy.

Crystal structure analysis of Form A of (−)-(1R,2R)-3-(3-dimethylamino-1-ethyl-2-methylpropyl)-phenol hydrochloride showed monoclinic crystals with the following parameters of the elemental cell (length of side and angle):
a: 7.11 Å
b: 11.62 Å
c: 17.43 Å
β: 95.0°.

The elemental cell of the crystal of crystalline Form A has a volume of 1434±5 $Å^3$ and a calculated density of 1.20±0.01 $g/cm^3$.

The invention further relates to processes for the preparation of crystalline Form A of (−)-(1R,2R)-3-(3-dimethylamino-1-ethyl-2-methylpropyl)-phenol hydrochloride.

The process starts from crystalline Form B of (−)-(1R,2R)-3-(3-dimethylamino-1-ethyl-2-methylpropyl)-phenol hydrochloride prepared according to U.S. Pat. No. 6,248,737 or 6,344,558 or European Patent EP 693 475 B1 incorporated herein by reference.

In one embodiment of the process (−)-(1R,2R)-3-(3-dimethylamino-1-ethyl-2-methylpropyl)-phenol hydrochloride of crystalline Form A is produced by dissolving the (−)-(1R,2R)-3-(3-dimethylamino-1-ethyl-2-methylpropyl)-phenol hydrochloride of crystalline Form B in acetone, acetonitrile or isopropanol, optionally followed by filtering, leaving the solution to crystallize and isolating the crystals of (−)-(1R,2R)-3-(3-dimethylamino-1-ethyl-2-methylpropyl)-phenol hydrochloride of crystalline Form A preferably by filtering again.

If acetone or acetonitrile is used it is preferred that during this process the temperature is kept below +40° C., more preferably below +25° C., especially after filtering. It is further preferred that in this process between 5 mg and 1 mg, more preferably between 2.5 mg and 1.4 mg, especially between 2.0 mg and 1.4 mg (−)-(1R,2R)-3-(3-dimethylamino-1-ethyl-2-methylpropyl)-phenol hydrochloride is dissolved per ml solvent.

The use of isopropanol is preferred, if seed crystals of (−)-(1R,2R)-3-(3-dimethylamino-1-ethyl-2-methylpropyl)-phenol hydrochloride of crystalline Form A are available. The isopropanol used preferably contains about 0.5% per volume of water. The dissolution of the (−)-(1R,2R)-3-(3-dimethylamino-1-ethyl-2-methylpropyl)-phenol hydrochloride of crystalline Form B in isopropanol is performed at temperatures above room temperature, preferably above 65° C. but not exceeding 80° C. After complete dissolution the heat is turned of and the seed crystals are added during a first cooling phase. Thereafter the resulting mixture is cooled down to $\leq 15°$ C., preferably $\leq 10°$ C. and especially $\leq 5°$ C.

Optionally it is possible to reduce the solvent by evaporation, preferably in an evaporator under reduced pressure. Preferably the remaining volume of the solution after evaporation should not be less than 20% of the volume at the beginning of the process. Optionally it is also possible to add active carbon to the solution originally prepared.

In a preferred embodiment of the invention the (−)-(1R,2R)-3-(3-dimethylamino-1-ethyl-2-methylpropyl)-phenol hydrochloride of crystalline Form A obtained by the process described above is redesolved in acetone acetonitrile or isopropanol, preferably in the solvent already used in the first step, optionally is filtered to remove any insoluble residue and, optionally after reducing the amount of solvent by evaporation, is left to crystallize.

It is preferred that in the last crystallization step the temperature is maintained at $\leq 15°$ C., more preferably $\leq 10°$ C. and especially $\leq 5°$ C.

In a further embodiment of the process according to the invention (−)-(1R,2R)-3-(3-dimethylamino-1-ethyl-2-methylpropyl)-phenol hydrochloride of crystalline Form A is produced in the solid state by cooling (−)-(1R,2R)-3-(3-dimethylamino-1-ethyl-2-methylpropyl)-phenol hydrochloride of crystalline Form B between 24 h and 168 h to a temperature between −4° C. and −80° C. It is preferred that in this process the cooling temperature is between −10° C. and −60° C., preferably between −15° C. and −50° C., especially between −25° C. and −40° C. and the cooling is carried out for a time between 24 h and 120 h, preferably between 24 h and 72 h, especially between 24 h and 48 h.

This invention further relates to a new Crystalline Form A of (−)-(1R,2R)-3-(3-dimethylamino-1-ethyl-2-methylpropyl)-phenol hydrochloride obtainable by dissolving (−)-(1R,2R)-3-(3-dimethylamino-1-ethyl-2-methylpropyl)-phenol hydrochloride of Form B in acetonitrile together with active carbon, heating the solution to the boiling point, removing the active carbon by filtering, stirring the solution at a temperature below 40° C., removing insoluble residue by filtering and removing part of the solvent leaving (−)-(1R,2R)-3-(3-dimethylamino-1-ethyl-2-methylpropyl)-phenol hydrochloride of Form A to crystallize, redissolving the crystals so obtained in acetonitrile, removing insoluble residue by filtering and removing part of the solvent leaving (−)-(1R,2R)-3-(3-dimethylamino-1-ethyl-2-methylpropyl)-phenol hydrochloride of Form A to crystallize.

Crystalline Form A according to the invention has the same pharmacological activity as Form B but is more stable under ambient conditions. It can be advantageously used as active ingredient in pharmaceutical compositions.

Therefore the invention further relates to a pharmaceutical composition containing as active ingredient (−)-(1R,2R)-3-(3-dimethylamino-1-ethyl-2-methylpropyl)-phenol hydrochloride of crystalline Form A according to the invention and at least one suitable additive and/or auxiliary substance.

Such pharmaceutical composition according to the invention contains, in addition to crystalline Form A (−)-(1R,2R)-3-(3-dimethylamino-1-ethyl-2-methylpropyl)-phenol hydrochloride, one or more suitable additive and/or auxiliary substance such as for example carrier materials, fillers, solvents, diluents, coloring agents and/or binders, and may be administered as liquid medicament preparations in the form of injectable solutions, drops or juices, as semi-solid medicament preparations in the form of granules, tablets, pellets, patches, capsules, plasters or aerosols. The choice of the auxiliary substances, etc., as well as the amounts thereof to be used depend on whether the medicament is to be administered orally, per orally, parenterally, intravenously, intraperitoneally, intradermally, intramuscularly, intranasally, buccally, rectally or topically, for example to the skin, the mucous membranes or the eyes. For oral application suitable preparations are in the form of tablets, sugar-coated pills, capsules, granules, droplets, juices and syrups, while for parenteral, topical and inhalative application suitable forms are solutions, suspensions, readily reconstitutable dry preparations, as well as sprays. Form A in a depot form, in dissolved form or in a plaster, optionally with the addition of agents promoting skin penetration, are suitable percutaneous application preparations. Preparation forms that can be administered orally or percutaneously can provide for the delayed release of crystalline Form A according to the invention. In principle further active constituents known to the person skilled in the art may be added to the medicaments according to the invention.

Preferred formulations for crystalline Form A (−)-(1R,2R)-3-(3-dimethylamino-1-ethyl-2-methylpropyl)-phenol hydrochloride according to the invention are presented in the PCT-application WO 03/035054 incorporated herein by reference.

The amount of active constituent to be administered to the patient varies depending on the patient's weight, on the type of application, medical indication and severity of the condition. Normally 0.005 to 1000 mg/kg, preferably 0.05 to 5 mg/kg of crystalline Form A according to the invention are administered.

Preferably, the crystalline Form A according to the invention is used for the treatment of pain or the treatment of urinary incontinence. Accordingly the invention also relates to the use of crystalline Form A according to the invention for the treatment of pain or the treatment of urinary incontinence.

Additionally the invention relates to a method of treatment using a sufficient amount of crystalline Form A according to the invention for the treatment of a disease, especially pain or urinary incontinence.

Certain embodiments of the present invention may be further understood by reference to the following specific examples. These examples and the terminology used herein are for the purpose of describing particular embodiments only and are not intended to be limiting.

Example 1

Master Recipe for Preparation of Form A

The master recipe is valid for a 50 ml scale.
Provide 1.9 g (−)-(1R,2R)-3-(3-dimethylamino-1-ethyl-2-methylpropyl)-phenol hydrochloride prepared according to example 25 of European Patent EP 693 475 B1 in a 50 ml glass round bottom vessel with a 3-blade overhead stirrer with baffles.
Add 25 ml isopropanol and 0.5% (v/v) water
Stir at 800 rpm
Heat to 80° C.
Hold temperature while stirring for 10 minutes
Cool to 65° C.
Add 0.056 g seeds (Mean Sq. Wt. CL=58 $\mu m^2$, Median No Wt. CL=22 $\mu m$)
Cool to 0° C. over 1 hour
Filter slurry through PTFE filter column (5 $\mu m$ pore size)
Dry solid material under slight vacuum until constant weight (approx. 24 hours)
Repeat the same procedure with the dry solid material obtained Example 2

Preparation of Form A (1)

(−)-(1R,2R)-3-(3-dimethylamino-1-ethyl-2-methylpropyl)-phenol hydrochloride was prepared according to example 25 of European Patent EP 693 475 B1. 32.2 mg of the thus synthesized (−)-(1R,2R)-3-(3-dimethylamino-1-ethyl-2-methylpropyl)-phenol hydrochloride was—by slight heating up to 40° C. and/or agitating on an orbital shaker for 30 min—dissolved in 20 ml acetone. Following that the solution was filtered through a nylon syringe filter having a mesh of 0.20 $\mu m$ and the solution was left to crystallize by slow evaporation of the solvent. Crystalline Form A of (−)-(1R,2R)-3-(3-dimethylamino-1-ethyl-2-methylpropyl)-phenol hydrochloride was generated as proven by X-ray powder diffraction and by RAMAN microscopic analysis.

Example 3

Preparation of Form A (2)

(−)-(1R,2R)-3-(3-dimethylamino-1-ethyl-2-methylpropyl)-phenol hydrochloride was prepared according to example 25 of European Patent EP 693 475 B1. 32.2 mg of the thus synthesized (−)-(1R,2R)-3-(3-dimethylamino-1-ethyl-2-methylpropyl)-phenol hydrochloride was—if necessary by agitating for e.g. 30 min—dissolved in 20 ml acetone. Following that the solution was filtered with a nylon syringe filter having a mesh of 0.20 $\mu m$ and the solution was left to crystallize by slow evaporation of the solvent. In no step after and including the dissolving the temperature was allowed to rise above +25° C. Crystalline Form A of (−)-(1R,2R)-3-(3-dimethylamino-1-ethyl-2-methylpropyl)-phenol hydrochloride was generated as proven by X-ray powder diffraction experiment and by RAMAN microscopic analysis.

Example 4

Preparation of Form A (3)

(−)-(1R,2R)-3-(3-dimethylamino-1-ethyl-2-methylpropyl)-phenol hydrochloride was prepared according to example 25 of European Patent EP 693 475 B1. 350 mg of the thus synthesized (−)-(1R,2R)-3-(3-dimethylamino-1-ethyl-2-methylpropyl)-phenol hydrochloride were dissolved in 50 ml acetonitrile in a 250 ml flask. The mixture was stirred for 1.5 h on a water bath heated to 37° C.±1° C. Any insoluble residue was removed by filtering. Of the clear solution 35 ml was removed on a rotation evaporator at 70-80 mbar and a temperature of the water bath of 30° C.±1° C. The precipitated solid compound was filtered by vacuum. Crystalline Form A of (−)-(1R,2R)-3-(3-dimethylamino-1-ethyl-2-methylpropyl)-phenol hydrochloride was generated as proven by X-ray powder diffraction and by RAMAN microscopic analysis.

Example 5

Preparation of Form A (4)

(−)-(1R,2R)-3-(3-dimethylamino-1-ethyl-2-methylpropyl)-phenol hydrochloride was prepared according to example 25 of European Patent EP 693 475 B1. The thus synthesized (−)-(1R,2R)-3-(3-dimethylamino-1-ethyl-2-methylpropyl)-phenol hydrochloride was stored for 72 h at −40° C. Crystalline Form A of (−)-(1R,2R)-3-(3-dimethylamino-1-ethyl-2-methylpropyl)-phenol hydrochloride was generated as proven by X-ray powder diffraction and by RAMAN microscopic analysis.

Example 6

Preparation of Form A (5)

$C_{14}H_{24}ClNO$
Mol. Wt.: 257,80

Recrystalization in Acetonitrile →

$C_{14}H_{24}ClNO$
Mol. Wt.: 257,80

(−)-(1R,2R)-3-(3-dimethylamino-1-ethyl-2-methylpropyl)-phenol hydrochloride was prepared according to example 25 of European Patent EP 693 475 B1. 370 mg of the thus synthesized (−)-(1R,2R)-3-(3-dimethylamino-1-ethyl-2-methylpropyl)-phenol hydrochloride were added to 40 ml acetonitrile and 100 mg active carbon in a 100 ml flask and heated to the boiling point. The active carbon was filtered off from the hot solution by means of a paper filter and the filtrate concentrated to a volume of approx. 10 ml in a rotation evaporator at 150±10 mbar and 50° C. The solution was slowly rotated for 30 minutes at room temperature. Following that the solution was allowed to stand for 30 minutes at room temperature and than for 1 hour at 4° C. The Crystals are filtered by vacuum through a glass filter (276 mg yield).

266 mg of these Crystals were dissolved at room temperature in 45 ml acetonitrile, insoluble residues were removed by filtration and the solution was rotated for 1.5 h at 35-40° C. at atmospheric pressure in a rotation evaporator. Than the solution was concentrated at 50° C. and 150±10 mbar to a volume of approx. 10 ml and then slowly rotated for 30 minutes at room temperature. Following that the flask was allowed to stand for 12 h at 4° C.

The precipitated solid is filtered by vacuum through a glass filter and dried in the air.

Yield:

151 mg (40.8% of the theory in relation to used educt), white microcrystalline solid form

Example 7

Preparation of Form B (1)

(−)-(1R,2R)-3-(3-dimethylamino-1-ethyl-2-methylpropyl)-phenol hydrochloride was prepared according to example 25 of European Patent EP 693 475 B1. Crystalline Form B of (−)-(1R,2R)-3-(3-dimethylamino-1-ethyl-2-methylpropyl)-phenol hydrochloride was generated as proven by X-ray powder diffraction and by RAMAN microscopic analysis.

Example 8

Preparation of Form B (2)

(−)-(1R,2R)-3-(3-dimethylamino-1-ethyl-2-methylpropyl)-phenol hydrochloride prepared according to one of the examples 1 to 5 was milled for at least 20 min. Then it was kept at 130° C. in an oven for 80 min. Crystalline Form B of (−)-(1R,2R)-3-(3-dimethylamino-1-ethyl-2-methylpropyl)-phenol hydrochloride was generated as proven by X-ray powder diffraction and by RAMAN microscopic analysis.

Example 9

Preparation of Form B (3)

(−)-(1R,2R)-3-(3-dimethylamino-1-ethyl-2-methylpropyl)-phenol hydrochloride prepared according to one of the examples 1 to 5 was cryogrinded for at least 15 min. Then it was kept at 125° C. in a TGA for 30 min. Crystalline Form B of (−)-(1R,2R)-3-(3-dimethylamino-1-ethyl-2-methylpropyl)-phenol hydrochloride was generated as proven by X-ray powder diffraction and by RAMAN microscopic analysis.

Example 10

X-Ray Powder Diffraction Patterns of Forms A (1) and B (1)

Powder Data Collection was performed with a STOE Stadi P Transmission Powder Diffractometer equipped with a curved germanium monochromator and a linear position sensitive detector. The very carefully ground powders were prepared as flat samples. As source of the beam a copper X-ray tube with monochromatized Cu K$_{\alpha 1}$ ($\lambda$=1.54051 Å) radiation generated at 50 kV and 30 mA was used. The 2θ area for the measurement was 5°-40°. The used step width was 0.02 degrees in 2 theta. The data were collected at a temperature of 23±1°.

The X-ray pattern for Form A is shown in FIG. 1, the X-ray pattern for Form B in FIG. 4.

The data are shown in Table 1.

TABLE 1

Peak and Relative Intensity Listing (°2θ, peaks with I/I1 value of 10 and over)

| Peak No. | A | I/I1 | B | I/I1 |
|---|---|---|---|---|
| 1 | 9.07 | 10 | 14.58 | 100 |
| 2 | 10.11 | 9 | 14.94 | 9 |
| 3 | 14.51 | 100 | 15.42 | 19 |
| 4 | 15.08 | 24 | 15.76 | 27 |
| 5 | 15.39 | 11 | 16.05 | 8 |
| 6 | 15.69 | 22 | 16.77 | 14 |
| 7 | 15.96 | 24 | 18.01 | 60 |
| 8 | 16.62 | 13 | 19.60 | 39 |
| 9 | 17.00 | 20 | 20.18 | 27 |
| 10 | 18.24 | 63 | 20.98 | 19 |
| 11 | 18.88 | 28 | 21.43 | 14 |
| 12 | 20.00 | 23 | 21.99 | 65 |
| 13 | 20.39 | 47 | 23.71 | 4 |
| 14 | 21.66 | 47 | 24.73 | 43 |
| 15 | 22.54 | 41 | 25.10 | 14 |
| 16 | 24.27 | 28 | 25.71 | 21 |
| 17 | 25.03 | 13 | 26.29 | 10 |
| 18 | 25.47 | 43 | 26.81 | 5 |
| 19 | 25.84 | 20 | 27.76 | 20 |
| 20 | 26.04 | 27 | 28.19 | 39 |
| 21 | 26.94 | 13 | 29.20 | 12 |
| 22 | 27.29 | 29 | 29.86 | 13 |
| 23 | 27.63 | 28 | 30.28 | 5 |
| 24 | 28.33 | 20 | 30.58 | 6 |
| 25 | 28.72 | 12 | 31.15 | 22 |
| 26 | 29.09 | 12 | 32.41 | 6 |
| 27 | 29.29 | 21 | 32.91 | 5 |
| 28 | 29.76 | 11 | 33.17 | 6 |
| 29 | 30.37 | 23 | 34.34 | 6 |
| 30 | 30.74 | 11 | 35.88 | 9 |
| 31 | 31.70 | 14 | 36.29 | 7 |
| 32 | 34.37 | 11 | 39.08 | 9 |

Example 11

IR Spectrum of Forms A and B

The mid IR spectra were acquired on a Nicolet model 860 Fourier transform IR spectrophotometer equipped with a globar source, Ge/KBr beamsplitter, and deterated triglycine sulfate (DTGS) detector. A Spectra-Tech, Inc. diffuse reflectance accessory was utilized for sampling. Each spectrum represents 256 co-added scans at a spectral resolution of 4 cm$^{-1}$. A background data set was then acquired with an alignment mirror in place. A single beam sample data set was then acquired. Subsequently, a Log 1/R (R=Reflectance) spectrum was acquired by rationing the two data sets against each other.

The spectrophotometer was calibrated (wavelength) with polystyrene at the time of use.

The spectrum for Form A is shown in FIG. 2. The spectrum for Form B is shown in FIG. 5.

The data are shown in the following Table 2.

TABLE 2

IR Peak Listing

| Form A | | Form B | |
|---|---|---|---|
| Peak Pos. (cm$^{-1}$) | Intensity (log 1/R) | Peak Pos. (cm$^{-1}$) | Intensity (log 1/R) |
| 3180.4 | 1.878 | 3170.2 | 2.196 |
| 2970 | 1.856 | 3013.1 | 1.791 |
| 1462.1 | 1.848 | 2962.5 | 2.098 |
| 2695.2 | 1.841 | 2933.4 | 1.945 |
| 1600.9 | 1.838 | 2682 | 2.116 |
| 1281.6 | 1.771 | 1940.5 | 1.242 |
| 1378.3 | 1.763 | 1870.7 | 1.246 |
| 1219.9 | 1.754 | 1801.7 | 1.201 |
| 1181.2 | 1.748 | 1749.5 | 1.236 |
| 1503.6 | 1.743 | 1598.1 | 2.138 |
| 1256.5 | 1.734 | 1503.2 | 1.755 |
| 712.6 | 1.725 | 1451.5 | 2.164 |
| 879.8 | 1.713 | 1417.2 | 1.89 |
| 684.7 | 1.692 | 1396.3 | 1.843 |
| 798.7 | 1.681 | 1377.1 | 1.864 |
| 1313.6 | 1.673 | 1353.2 | 1.726 |
| 1005.1 | 1.655 | 1313.2 | 1.661 |
| 731.2 | 1.63 | 1280.7 | 1.977 |
| 1090.9 | 1.626 | 1254.8 | 1.973 |
| 810.2 | 1.622 | 1217.6 | 2.015 |
| 971.5 | 1.588 | 1177.5 | 1.868 |
| 842.6 | 1.576 | 1154.6 | 1.597 |
| 831.7 | 1.574 | 1136.4 | 1.431 |
| 1111.5 | 1.55 | 1111.3 | 1.512 |
| 1049.8 | 1.534 | 1090.3 | 1.625 |
| 1136.5 | 1.498 | 1065.9 | 1.425 |
| 461.3 | 1.476 | 1049.9 | 1.52 |
| 1065.8 | 1.457 | 1004.6 | 1.813 |
| 495.1 | 1.438 | 958.7 | 1.855 |
| 542.1 | 1.408 | 946.6 | 1.735 |
| 595.8 | 1.384 | 912.5 | 1.292 |
| 527.9 | 1.327 | 877.8 | 1.951 |
| 912.4 | 1.304 | 842.7 | 1.657 |
| 1032.4 | 1.3 | 831.4 | 1.664 |
| 416.9 | 1.287 | 810.7 | 1.715 |
| 1698.3 | 1.282 | 795.2 | 1.892 |
| 1940.5 | 1.279 | 730.6 | 1.855 |
| 1870.6 | 1.277 | 711.7 | 2.04 |
| 1749.4 | 1.268 | 683.4 | 1.917 |
| 1801.6 | 1.208 | 595.6 | 1.439 |
| 2115.5 | 1.061 | 542.1 | 1.497 |
| | | 527.7 | 1.425 |
| | | 495.1 | 1.663 |
| | | 464.4 | 1.622 |
| | | 416.7 | 1.439 |

Example 12

Single Crystal Structure Analysis of Form A

A colorless crystal of (−)-(1R,2R)-3-(3-dimethylamino-1-ethyl-2-methylpropyl)-phenol hydrochloride prepared according to one of the examples 2 to 6 having approximate dimensions of 0.6×0.60×0.50 mm was mounted on a glass fiber in random orientation. Preliminary examination and data collection were performed with Cu K$_\alpha$ radiation (1.54184 Å) on a Enraf-Nonius CAD4 computer controlled kappa axis diffractometer equipped with a graphite crystal, incident beam monochromator.

Cell constants and an orientation matrix for data collection were obtained from least-squares refinement using the setting angles of 25 reflections in the range 16°<θ<24°, measured by the computer controlled diagonal slit method of centering. The monoclinic cell parameters and calculated volume are: a=7.110(3), b=11.615(4), c=17.425(6) Å, β=95.00(3), V=1433.5(10) Å$^3$. For Z=4 and formula weight of 257.79 the calculated density is 1.20 g·cm$^{-3}$. The space group was determined to be P2$_1$ (No. 19).

The data were collected at a temperature of −103±5° C. using ω-θ scan technique. The scan rate varied from 4 to 20°/min (in ω). The variable scan rate allows rapid data collection for intense reflections where a fast scan rate is used and assures good counting statistics for weak reflections where a slow scan rate is used. Data were collected to a maximum of 2θ of 75.11°. The scan range)(in ° was determined as a function of θ to correct for the separation of the Kα doublet. The scan width was calculated as follows:

$$\theta \text{ scan width}=0.8+0.140 \tan \theta$$

Moving-crystal moving-counter background counts were made by scanning an additional 25% above and below this range. Thus the ratio of peak counting time to background counting time was 2:1. The counter aperture was also adjusted as a function of θ. The horizontal aperture width ranged from 2.4 to 2.5 mm; the vertical aperture was set at 4.0 mm.

The data for Form A as collected in a commonly known ".cif"-document for complete reference of distances within the molecule are shown in Table 3.

TABLE 3

Table 3a.
Crystal data and structure refinement for Form_A.

| Identification code | FormA |
|---|---|
| Empirical formula | C14H24ClNO |
| Formula weight | 257.79 |
| Temperature | 170(2) K |
| Wavelength | 1.54184 Å |
| Crystal system | monoclinic |
| Space group | P 21 |
| Unit cell dimensions | a = 7.110(3) Å    alpha = 90 deg. |
| | b = 11.615(4) Å    beta = 95.00(3) deg. |
| | c = 17.425(6) Å    gamma = 90 deg. |
| Volume | 1433.5(10) Å$^3$ |
| Z | 4 |
| Density (calculated) | 1.195 Mg/m$^3$ |
| Absorption coefficient | 2.230 mm$^{-1}$ |
| F(000) | 560 |
| Theta range for data collection | 4.58 to 75.11 deg. |
| Index ranges | 0 <= h <= 8, −14 <= k <= 14, −21 <= l <= 21 |
| Reflections collected | 4531 |
| Independent reflections | 4531 [R(int) = 0.0000] |
| Refinement method | Full-matrix least-squares on F$^2$ |
| Data/restraints/parameters | 4531/1/323 |
| Goodness-of-fit on F$^2$ | 1.035 |
| Final R indices [I > 2sigma(I)] | R1 = 0.0588, wR2 = 0.1629 |
| R indices (all data) | R1 = 0.0643, wR2 = 0.1673 |
| Absolute structure parameter | .027(19) |
| Largest diff. peak and hole | 0.686 and −0.696 e · Å$^{-3}$ |

Table 3b.
Atomic coordinates (×10$^4$) and equivalent isotropic displacement parameters (Å$^2$ × 10$^3$) for Form_A. U(eq) is defined as one third of the trace of the orthogonalized Uij tensor.

| | x | y | z | U(eq) |
|---|---|---|---|---|
| Cl(1) | 2148(1) | 3541(1) | 9878(1) | 29(1) |
| Cl(2) | 7279(1) | 2551(1) | 5089(1) | 28(1) |
| O(1) | −588(5) | 5289(3) | 9077(2) | 36(1) |
| N(1) | 822(5) | 3979(3) | 4964(2) | 22(1) |
| O(2) | 4799(4) | 769(3) | 5795(2) | 36(1) |
| N(2) | 5722(5) | 2083(3) | 10053(2) | 27(1) |
| C(1) | 2263(6) | 3215(4) | 4667(2) | 33(1) |

TABLE 3-continued

| | | | | | |
|---|---|---|---|---|---|
| C(2) | −85(6) | 4736(4) | 4336(2) | 31(1) | |
| C(3) | 1580(5) | 4713(3) | 5628(2) | 22(1) | |
| C(4) | 2627(5) | 4056(3) | 6291(2) | 21(1) | |
| C(5) | 1401(6) | 3130(4) | 6613(2) | 29(1) | |
| C(6) | 3437(5) | 4902(3) | 6925(2) | 22(1) | |
| C(7) | 4927(5) | 5729(4) | 6656(2) | 27(1) | |
| C(8) | 6603(6) | 5138(4) | 6351(3) | 38(1) | |
| C(9) | 1930(5) | 5552(3) | 7326(2) | 21(1) | |
| C(10) | 1188(6) | 6603(3) | 7050(2) | 25(1) | |
| C(11) | −137(6) | 7175(3) | 7448(2) | 28(1) | |
| C(12) | −739(6) | 6733(4) | 8117(2) | 28(1) | |
| C(13) | −19(6) | 5686(4) | 8404(2) | 26(1) | |
| C(14) | 1313(5) | 5102(3) | 8001(2) | 23(1) | |
| C(20) | 7093(7) | 2841(5) | 10502(3) | 41(1) | |
| C(21) | 4877(7) | 1235(5) | 10570(3) | 41(1) | |
| C(22) | 6542(6) | 1458(3) | 9408(2) | 25(1) | |
| C(23) | 7484(5) | 2230(3) | 8856(2) | 22(1) | |
| C(24) | 6086(6) | 3070(4) | 8447(2) | 29(1) | |
| C(25) | 8541(5) | 1512(3) | 8274(2) | 20(1) | |
| C(26) | 10222(6) | 857(4) | 8681(2) | 28(1) | |
| C(27) | 11528(6) | 374(4) | 8118(3) | 36(1) | |
| C(28) | 7250(5) | 740(3) | 7756(2) | 22(1) | |
| C(29) | 6682(5) | −349(3) | 7991(2) | 24(1) | |
| C(30) | 5507(5) | −1019(3) | 7501(2) | 26(1) | |
| C(31) | 4871(6) | −654(3) | 6769(2) | 26(1) | |
| C(32) | 5427(6) | 430(4) | 6529(2) | 26(1) | |
| C(33) | 6604(5) | 1116(4) | 7018(2) | 24(1) | |

Table 3c.
Bond lengths [Å] and angles [deg] for Form_A.

| | |
|---|---|
| O(1)—C(13) | 1.355(5) |
| O(1)—H(1) | .86(11) |
| N(1)—C(1) | 1.482(5) |
| N(1)—C(3) | 1.499(5) |
| N(1)—C(2) | 1.504(5) |
| N(1)—H(1A) | .9100 |
| O(2)—C(32) | 1.374(5) |
| O(2)—H(2) | .90(9) |
| N(2)—C(20) | 1.485(6) |
| N(2)—C(21) | 1.495(6) |
| N(2)—C(22) | 1.497(5) |
| N(2)—H(2A) | .9100 |
| C(1)—H(1A) | .9801 |
| C(1)—H(1B) | .9801 |
| C(1)—H(1C) | .9801 |
| C(2)—H(2A) | .9801 |
| C(2)—H(2B) | .9801 |
| C(2)—H(2C) | .9801 |
| C(3)—C(4) | 1.524(5) |
| C(3)—H(3A) | .9800 |
| C(3)—H(3B) | .9800 |
| C(4)—C(5) | 1.522(5) |
| C(4)—C(6) | 1.553(5) |
| C(4)—H(4) | .9800 |
| C(5)—H(5A) | .9801 |
| C(5)—H(5B) | .9801 |
| C(5)—H(5C) | .9801 |
| C(6)—C(9) | 1.528(5) |
| C(6)—C(7) | 1.533(6) |
| C(6)—H(6) | .9800 |
| C(7)—C(8) | 1.511(6) |
| C(7)—H(7A) | .9800 |
| C(7)—H(7B) | .9800 |
| C(8)—H(8A) | .9801 |
| C(8)—H(8B) | .9801 |
| C(8)—H(8C) | .9801 |
| C(9)—C(14) | 1.392(5) |
| C(9)—C(10) | 1.398(5) |
| C(10)—C(11) | 1.386(6) |
| C(10)—H(10) | .9800 |
| C(11)—C(12) | 1.376(6) |
| C(11)—H(11) | .9800 |
| C(12)—C(13) | 1.395(6) |
| C(12)—H(12) | .9800 |
| C(13)—C(14) | 1.402(5) |
| C(14)—H(14) | .9800 |
| C(20)—H(20A) | .9801 |
| C(20)—H(20B) | .9801 |
| C(20)—H(20C) | .9801 |
| C(21)—H(21A) | .9801 |
| C(21)—H(21B) | .9801 |
| C(21)—H(21C) | .9801 |
| C(22)—C(23) | 1.513(5) |
| C(22)—H(22A) | .9800 |
| C(22)—H(22B) | .9800 |
| C(23)—C(24) | 1.525(5) |
| C(23)—C(25) | 1.556(5) |
| C(23)—H(23) | .9800 |
| C(24)—H(24A) | .9801 |
| C(24)—H(24B) | .9801 |
| C(24)—H(24C) | .9801 |
| C(25)—C(28) | 1.523(5) |
| C(25)—C(26) | 1.537(5) |
| C(25)—H(25) | .9800 |
| C(26)—C(27) | 1.517(5) |
| C(26)—H(26A) | .9800 |
| C(26)—H(26B) | .9800 |
| C(27)—H(27A) | .9801 |
| C(27)—H(27B) | .9801 |
| C(27)—H(27C) | .9801 |
| C(28)—C(33) | 1.397(5) |
| C(28)—C(29) | 1.400(6) |
| C(29)—C(30) | 1.382(6) |
| C(29)—H(29) | .9800 |
| C(30)—C(31) | 1.381(6) |
| C(30)—H(30) | .9800 |
| C(31)—C(32) | 1.395(6) |
| C(31)—H(31) | .9800 |
| C(32)—C(33) | 1.392(6) |
| C(33)—H(33) | .9800 |
| C(13)—O(1)—H(1) | 116(6) |
| C(1)—N(1)—C(3) | 113.4(3) |
| C(1)—N(1)—C(2) | 111.2(3) |
| C(3)—N(1)—C(2) | 109.4(3) |
| C(1)—N(1)—H(1A) | 107.5 |
| C(3)—N(1)—H(1A) | 107.5 |
| C(2)—N(1)—H(1A) | 107.5 |
| C(32)—O(2)—H(2) | 127(6) |
| C(20)—N(2)—C(21) | 110.7(4) |
| C(20)—N(2)—C(22) | 113.7(3) |
| C(21)—N(2)—C(22) | 109.6(3) |
| C(20)—N(2)—H(2A) | 107.5 |
| C(21)—N(2)—H(2A) | 107.5 |
| C(22)—N(2)—H(2A) | 107.5 |
| N(1)—C(1)—H(1A) | 109.5 |
| N(1)—C(1)—H(1B) | 109.5 |
| H(1A)—C(1)—H(1B) | 109.5 |
| N(1)—C(1)—H(1C) | 109.5 |
| H(1A)—C(1)—H(1C) | 109.5 |
| H(1B)—C(1)—H(1C) | 109.5 |
| N(1)—C(2)—H(2A) | 109.5 |
| N(1)—C(2)—H(2B) | 109.5 |
| H(2A)—C(2)—H(2B) | 109.5 |
| N(1)—C(2)—H(2C) | 109.5 |
| H(2A)—C(2)—H(2C) | 109.5 |
| H(2B)—C(2)—H(2C) | 109.5 |
| N(1)—C(3)—C(4) | 114.8(3) |
| N(1)—C(3)—H(3A) | 108.6 |
| C(4)—C(3)—H(3A) | 108.6 |
| N(1)—C(3)—H(3B) | 108.6 |
| C(4)—C(3)—H(3B) | 108.6 |
| H(3A)—C(3)—H(3B) | 107.6 |
| C(5)—C(4)—C(3) | 112.1(3) |
| C(5)—C(4)—C(6) | 111.9(3) |
| C(3)—C(4)—C(6) | 110.4(3) |
| C(5)—C(4)—H(4) | 107.4 |
| C(3)—C(4)—H(4) | 107.4 |
| C(6)—C(4)—H(4) | 107.4 |
| C(4)—C(5)—H(5A) | 109.5 |
| C(4)—C(5)—H(5B) | 109.5 |
| H(5A)—C(5)—H(5B) | 109.5 |
| C(4)—C(5)—H(5C) | 109.5 |
| H(5A)—C(5)—H(5C) | 109.5 |
| H(5B)—C(5)—H(5C) | 109.5 |
| C(9)—C(6)—C(7) | 111.2(3) |
| C(9)—C(6)—C(4) | 114.0(3) |
| C(7)—C(6)—C(4) | 113.7(3) |
| C(9)—C(6)—H(6) | 105.7 |
| C(7)—C(6)—H(6) | 105.7 |

TABLE 3-continued

| | |
|---|---|
| C(4)—C(6)—H(6) | 105.7 |
| C(8)—C(7)—C(6) | 114.2(4) |
| C(8)—C(7)—H(7A) | 108.7 |
| C(6)—C(7)—H(7A) | 108.7 |
| C(8)—C(7)—H(7B) | 108.7 |
| C(6)—C(7)—H(7B) | 108.7 |
| H(7A)—C(7)—H(7B) | 107.6 |
| C(7)—C(8)—H(8A) | 109.5 |
| C(7)—C(8)—H(8B) | 109.5 |
| H(8A)—C(8)—H(8B) | 109.5 |
| C(7)—C(8)—H(8C) | 109.5 |
| H(8A)—C(8)—H(8C) | 109.5 |
| H(8B)—C(8)—H(8C) | 109.5 |
| C(14)—C(9)—C(10) | 118.7(3) |
| C(14)—C(9)—C(6) | 119.0(3) |
| C(10)—C(9)—C(6) | 122.2(3) |
| C(11)—C(10)—C(9) | 119.9(4) |
| C(11)—C(10)—H(10) | 120.0 |
| C(9)—C(10)—H(10) | 120.0 |
| C(12)—C(11)—C(10) | 121.3(4) |
| C(12)—C(11)—H(11) | 119.3 |
| C(10)—C(11)—H(11) | 119.3 |
| C(11)—C(12)—C(13) | 119.8(4) |
| C(11)—C(12)—H(12) | 120.1 |
| C(13)—C(12)—H(12) | 120.1 |
| O(1)—C(13)—C(12) | 118.6(4) |
| O(1)—C(13)—C(14) | 122.3(4) |
| C(12)—C(13)—C(14) | 119.0(4) |
| C(9)—C(14)—C(13) | 121.2(3) |
| C(9)—C(14)—H(14) | 119.4 |
| C(13)—C(14)—H(14) | 119.4 |
| N(2)—C(20)—H(20A) | 109.5 |
| N(2)—C(20)—H(20B) | 109.5 |
| H(20A)—C(20)—H(20B) | 109.5 |
| N(2)—C(20)—H(20C) | 109.5 |
| H(20A)—C(20)—H(20C) | 109.5 |
| H(20B)—C(20)—H(20C) | 109.5 |
| N(2)—C(21)—H(21A) | 109.5 |
| N(2)—C(21)—H(21B) | 109.5 |
| H(21A)—C(21)—H(21B) | 109.5 |
| N(2)—C(21)—H(21C) | 109.5 |
| H(21A)—C(21)—H(21C) | 109.5 |
| H(21B)—C(21)—H(21C) | 109.5 |
| N(2)—C(22)—C(23) | 114.4(3) |
| N(2)—C(22)—H(22A) | 108.7 |
| C(23)—C(22)—H(22A) | 108.7 |
| N(2)—C(22)—H(22B) | 108.7 |
| C(23)—C(22)—H(22B) | 108.7 |
| H(22A)—C(22)—H(22B) | 107.6 |
| C(22)—C(23)—C(24) | 111.7(3) |
| C(22)—C(23)—C(25) | 111.3(3) |
| C(24)—C(23)—C(25) | 111.8(3) |
| C(22)—C(23)—H(23) | 107.3 |
| C(24)—C(23)—H(23) | 107.3 |
| C(25)—C(23)—H(23) | 107.3 |
| C(23)—C(24)—H(24A) | 109.5 |
| C(23)—C(24)—H(24B) | 109.5 |
| H(24A)—C(24)—H(24B) | 109.5 |
| C(23)—C(24)—H(24C) | 109.5 |
| H(24A)—C(24)—H(24C) | 109.5 |
| H(24B)—C(24)—H(24C) | 109.5 |
| C(28)—C(25)—C(26) | 112.8(3) |
| C(28)—C(25)—C(23) | 113.7(3) |
| C(26)—C(25)—C(23) | 111.4(3) |
| C(28)—C(25)—H(25) | 106.1 |
| C(26)—C(25)—H(25) | 106.1 |
| C(23)—C(25)—H(25) | 106.1 |
| C(27)—C(26)—C(25) | 112.3(3) |
| C(27)—C(26)—H(26A) | 109.1 |
| C(25)—C(26)—H(26A) | 109.1 |
| C(27)—C(26)—H(26B) | 109.1 |
| C(25)—C(26)—H(26B) | 109.1 |
| H(26A)—C(26)—H(26B) | 107.9 |
| C(26)—C(27)—H(27A) | 109.5 |
| C(26)—C(27)—H(27B) | 109.5 |
| H(27A)—C(27)—H(27B) | 109.5 |
| C(26)—C(27)—H(27C) | 109.5 |
| H(27A)—C(27)—H(27C) | 109.5 |
| H(27B)—C(27)—H(27C) | 109.5 |
| C(33)—C(28)—C(29) | 118.2(4) |
| C(33)—C(28)—C(25) | 119.6(3) |
| C(29)—C(28)—C(25) | 122.2(3) |
| C(30)—C(29)—C(28) | 120.1(4) |
| C(30)—C(29)—H(29) | 120.0 |
| C(28)—C(29)—H(29) | 120.0 |
| C(31)—C(30)—C(29) | 122.0(4) |
| C(31)—C(30)—H(30) | 119.0 |
| C(29)—C(30)—H(30) | 119.0 |
| C(30)—C(31)—C(32) | 118.4(4) |
| C(30)—C(31)—H(31) | 120.8 |
| C(32)—C(31)—H(31) | 120.8 |
| O(2)—C(32)—C(31) | 117.4(4) |
| O(2)—C(32)—C(33) | 122.3(4) |
| C(31)—C(32)—C(33) | 120.3(4) |
| C(28)—C(33)—C(32) | 121.1(4) |
| C(28)—C(33)—H(33) | 119.5 |
| C(32)—C(33)—H(33) | 119.5 |

Symmetry transformations used to generate equivalent atoms:
Table 3d.
Hydrogen coordinates ($\times 10^4$) and isotropic displacement parameters ($\text{Å}^2 \times 10^3$) for Form__A.

| | x | y | z | U(eq) |
|---|---|---|---|---|
| H(1) | −380(15) | 4570(10) | 9180(5) | 110(3) |
| H(1A) | −96 | 3523 | 5133 | 26 |
| H(2) | 5310(14) | 1310(9) | 5510(5) | 100(3) |
| H(2A) | 4770 | 2536 | 9841 | 32 |
| H(1A) | 1737 | 2848 | 4189 | 43 |
| H(1B) | 2630 | 2622 | 5051 | 43 |
| H(1C) | 3374 | 3671 | 4564 | 43 |
| H(2A) | 838 | 5299 | 4182 | 41 |
| H(2B) | −1162 | 5141 | 4525 | 41 |
| H(2C) | −523 | 4261 | 3891 | 41 |
| H(3A) | 525 | 5130 | 5827 | 29 |
| H(3B) | 2438 | 5287 | 5439 | 29 |
| H(4) | 3700 | 3668 | 6086 | 27 |
| H(5A) | 2110 | 2747 | 7048 | 38 |
| H(5B) | 1040 | 2563 | 6210 | 38 |
| H(5C) | 262 | 3484 | 6788 | 38 |
| H(6) | 4100 | 4422 | 7324 | 28 |
| H(7A) | 4328 | 6227 | 6252 | 35 |
| H(7B) | 5381 | 6223 | 7090 | 35 |
| H(8A) | 7580 | 5710 | 6270 | 49 |
| H(8B) | 6204 | 4761 | 5860 | 49 |
| H(8C) | 7111 | 4561 | 6723 | 49 |
| H(10) | 1604 | 6936 | 6577 | 32 |
| H(11) | −656 | 7908 | 7248 | 36 |
| H(12) | −1670 | 7153 | 8392 | 36 |
| H(14) | 1819 | 4364 | 8198 | 30 |
| H(20A) | 6484 | 3193 | 10927 | 54 |
| H(20B) | 7521 | 3445 | 10166 | 54 |
| H(20C) | 8179 | 2384 | 10710 | 54 |
| H(21A) | 4403 | 1642 | 11006 | 53 |
| H(21B) | 5842 | 677 | 10760 | 53 |
| H(21C) | 3833 | 830 | 10281 | 53 |
| H(22A) | 5532 | 1026 | 9118 | 32 |
| H(22B) | 7472 | 900 | 9629 | 32 |
| H(23) | 8433 | 2688 | 9162 | 29 |
| H(24A) | 5114 | 2639 | 8133 | 38 |
| H(24B) | 6755 | 3580 | 8115 | 38 |
| H(24C) | 5491 | 3530 | 8830 | 38 |
| H(25) | 9081 | 2070 | 7933 | 26 |
| H(26A) | 10938 | 1379 | 9040 | 37 |
| H(26B) | 9748 | 224 | 8982 | 37 |
| H(27A) | 10856 | −210 | 7794 | 46 |
| H(27B) | 12632 | 24 | 8403 | 46 |
| H(27C) | 11941 | 997 | 7792 | 46 |
| H(29) | 7118 | −637 | 8505 | 31 |
| H(30) | 5114 | −1776 | 7677 | 34 |
| H(31) | 4048 | −1144 | 6428 | 34 |
| H(33) | 6986 | 1876 | 6842 | 31 |

TABLE 3-continued

Table 3e.
Anisotropic displacement parameters ($Å^2 \times 10^3$) for Form_A.
The anisotropic displacement factor exponent takes the form:
$-2 pi^2 [h^2 a^{*2} U11 + \ldots + 2 h k a^* b^* U12]$

| | U11 | U22 | U33 | U23 | U13 | U12 |
|---|---|---|---|---|---|---|
| Cl(1) | 23(1) | 27(1) | 36(1) | −3(1) | −1(1) | 4(1) |
| Cl(2) | 23(1) | 25(1) | 35(1) | −2(1) | −2(1) | −5(1) |
| O(1) | 35(2) | 41(2) | 33(2) | 7(1) | 8(1) | 13(1) |
| N(1) | 19(2) | 28(2) | 18(1) | 1(1) | −4(1) | −5(1) |
| O(2) | 33(2) | 52(2) | 21(1) | 5(1) | −11(1) | −12(2) |
| N(2) | 22(2) | 31(2) | 27(2) | 2(1) | 2(1) | 8(1) |
| C(1) | 29(2) | 44(2) | 26(2) | −6(2) | 1(2) | 6(2) |
| C(2) | 25(2) | 41(2) | 26(2) | 11(2) | −8(2) | −4(2) |
| C(3) | 20(2) | 20(2) | 26(2) | 2(1) | −4(1) | −4(1) |
| C(4) | 19(2) | 23(2) | 20(2) | −1(1) | −2(1) | 3(1) |
| C(5) | 33(2) | 25(2) | 28(2) | 2(2) | −3(2) | −4(2) |
| C(6) | 17(2) | 26(2) | 20(2) | −2(1) | −6(1) | 6(1) |
| C(7) | 18(2) | 30(2) | 32(2) | −10(2) | −6(1) | 0(2) |
| C(8) | 20(2) | 40(2) | 54(3) | −11(2) | 5(2) | −3(2) |
| C(9) | 18(2) | 26(2) | 19(2) | −6(1) | −7(1) | 1(1) |
| C(10) | 23(2) | 24(2) | 26(2) | 0(2) | −4(1) | 1(1) |
| C(11) | 23(2) | 28(2) | 32(2) | 0(2) | −9(2) | 5(2) |
| C(12) | 20(2) | 31(2) | 32(2) | −5(2) | −1(2) | 5(2) |
| C(13) | 22(2) | 33(2) | 24(2) | 0(2) | −2(1) | 3(2) |
| C(14) | 20(2) | 24(2) | 25(2) | 0(2) | −5(1) | 5(1) |
| C(20) | 40(3) | 51(3) | 32(2) | −12(2) | −3(2) | −1(2) |
| C(21) | 39(3) | 49(3) | 37(2) | 10(2) | 16(2) | 10(2) |
| C(22) | 27(2) | 23(2) | 25(2) | −1(2) | 2(2) | 2(2) |
| C(23) | 21(2) | 22(2) | 22(2) | −2(1) | −3(1) | 2(1) |
| C(24) | 32(2) | 27(2) | 27(2) | 2(2) | −1(2) | 8(2) |
| C(25) | 15(2) | 24(2) | 20(2) | 1(1) | −3(1) | 1(1) |
| C(26) | 21(2) | 33(2) | 30(2) | −2(2) | −4(2) | 6(2) |
| C(27) | 25(2) | 39(2) | 43(2) | 1(2) | 4(2) | 7(2) |
| C(28) | 18(2) | 27(2) | 21(2) | −1(2) | 1(1) | 5(2) |
| C(29) | 22(2) | 25(2) | 25(2) | −1(2) | 1(1) | 3(1) |
| C(30) | 24(2) | 22(2) | 33(2) | −4(2) | 6(2) | −1(2) |
| C(31) | 19(2) | 31(2) | 28(2) | −10(2) | 1(1) | −2(2) |
| C(32) | 21(2) | 35(2) | 21(2) | −2(2) | 2(1) | −2(2) |
| C(33) | 17(2) | 30(2) | 25(2) | 1(2) | 1(1) | −4(1) |

Example 13

Single Crystal Structure Analysis of Form B

A colorless chunk of (−)-(1R,2R)-3-(3-dimethylamino-1-ethyl-2-methylpropyl)-phenol hydrochloride prepared according to one of the examples 7 to 9 having approximate dimensions of 0.44×0.40×0.35 mm was mounted on a glass fiber in random orientation. Preliminary examination and data collection were performed with Mo $K_\alpha$ radiation ($\lambda$=0.71073 Å) on a Nonius KappaCCD diffractometer.

Cell constants and an orientation matrix for data collection were obtained from least-squares refinement using the setting angles of 6172 reflections in the range 5<θ<27°. The orthorhombic cell parameters and calculated volume are: a=7.0882(3), b=11.8444(6), c=17.6708(11) Å, V=1483.6(2) $Å^3$. For Z=4 and formula weight of 257.79 the calculated density is 1.15 g·$cm^{-3}$. The refined mosaicity from DENZO/SCALEPACK was 0.68° (<1 mod, <2 poor) indicating moderate crystal quality. The space group was determined by the program ABSEN. From the systematic presence of:

h00 h=2n
0k0 k=2n
00l l=2n and from subsequent least-squares refinement, the space group was determined to be $P2_12_12_1$ (number 19).

The data were collected to a maximum 2θ value of 55.0°, at a temperature of 343±1 K.

The data from examples 12 and 13 are compared in Table 3f:

TABLE 3f

| | Form A (monoklin) | Form B (orthorhombic) |
|---|---|---|
| Formula | C14 H24 Cl N O | C14 H24 Cl N O |
| M.W./g/mol | 257.79 | 257.79 |
| Space group | No. 4, $P2_1$ | No. 19, $P2_12_12_1$ |
| Z (No. of Units) | 4 | 4 |
| a/Å | 7.110(3) | 7.0882(3) |
| b/Å | 11.615(4) | 11.8444(6) |
| c/Å | 17.425(6) | 17.6708(11) |
| α/° | 90 | 90 |
| β/° | 95.00(3) | 90 |
| γ/° | 90 | 90 |
| Volume of elementary cell/$Å^3$ | 1434 | 1484 |
| Density (calc.)/g/$cm^3$ | 1.20 | 1.15 |

The data for Form B as collected in a commonly known ".cif"-document for complete reference of distances within the molecule are shown below Table 4:

TABLE 4

Table 4a.
Crystal data and structure refinement for Form_B.

| | |
|---|---|
| Identification code | FormB |
| Empirical formula | C14H2H22ClNO |
| Formula weight | 257.79 |
| Temperature | 343 K |
| Wavelength | .71073 Å |
| Crystal system | orthorhombic |
| Space group | P 21 21 21 |
| Unit cell dimensions | a = 7.0882(3) Å   alpha = 90 deg. |
| | b = 11.8444(6) Å   beta = 90 deg. |
| | c = 17.6708(11) Å   gamma = 90 deg. |
| Volume | 1483.56(13) $Å^3$ |
| Z | 4 |
| Density (calculated) | 1.154 Mg/$m^3$ |
| Absorption coefficient | 0.244 $mm^{-1}$ |
| F(000) | 560 |
| Theta range for data collection | 5.04 to 27.49 deg. |
| Index ranges | −9 <= h <= 9, −15 <= k <= 15, −22 <= l <= 22 |
| Reflections collected | 3207 |
| Independent reflections | 3207 [R(int) = 0.0000] |
| Refinement method | Full-matrix least-squares on $F^2$ |
| Data/restraints/parameters | 3207/0/167 |
| Quality-of-fit on $F^2$ | 1.012 |
| Final R indices [I > 2sigma(I)] | R1 = 0.0440, wR2 = 0.1137 |
| R indices (all data) | R1 = 0.0598, wR2 = 0.1246 |
| Absolute structure parameter | −.03(8) |
| Extinction coefficient | .033(7) |
| Largest diff. peak and hole | 0.265 and −0.202 e · $Å^{-3}$ |

Table 4b.
Atomic coordinates ($\times 10^4$) and equivalent isotropic displacement parameters ($Å^2 \times 10^3$) for Form_B. U(eq) is defined as one third of the trace of the orthogonalized Uij tensor.

| | x | y | z | U(eq) |
|---|---|---|---|---|
| Cl | 7978(1) | −1959(1) | 7646(1) | 74(1) |
| O(33) | 4870(3) | 85(2) | 3443(1) | 94(1) |
| N(6) | 5522(3) | 1571(2) | 7545(1) | 64(1) |
| C(1) | 11558(4) | −160(3) | 5596(2) | 98(1) |
| C(2) | 10168(3) | 333(2) | 6149(2) | 75(1) |
| C(3) | 8514(3) | 925(2) | 5758(1) | 58(1) |
| C(4) | 7395(3) | 1654(2) | 6327(1) | 58(1) |
| C(5) | 6394(3) | 922(3) | 6909(1) | 64(1) |
| C(6) | 4611(5) | 782(3) | 8089(2) | 96(1) |
| C(7) | 6834(5) | 2342(3) | 7943(2) | 95(1) |
| C(31) | 7273(3) | 131(2) | 5286(1) | 57(1) |
| C(32) | 6643(3) | 472(2) | 4583(1) | 61(1) |
| C(33) | 5509(3) | −219(2) | 4138(1) | 68(1) |

TABLE 4-continued

| C(34) | 5050(3) | −1291(2) | 4395(2) | 74(1) |
|---|---|---|---|---|
| C(35) | 5679(4) | −1637(2) | 5098(2) | 75(1) |
| C(36) | 6782(3) | −946(2) | 5542(1) | 66(1) |
| C(41) | 6029(4) | 2461(2) | 5931(2) | 80(1) |

Table 4c.
Bond lengths [Å] and angles [deg] for Form__B.

| | |
|---|---|
| O(33)—H(33) | .76(3) |
| O(33)—C(33) | 1.358(3) |
| N(6)—H(6) | .82(2) |
| N(6)—C(7) | 1.481(4) |
| N(6)—C(6) | 1.488(3) |
| N(6)—C(5) | 1.496(3) |
| C(1)—C(2) | 1.505(4) |
| C(2)—C(3) | 1.531(3) |
| C(3)—C(31) | 1.534(3) |
| C(3)—C(4) | 1.546(3) |
| C(4)—C(5) | 1.520(3) |
| C(4)—C(41) | 1.530(3) |
| C(31)—C(32) | 1.381(3) |
| C(31)—C(36) | 1.396(3) |
| C(32)—C(33) | 1.391(3) |
| C(33)—C(34) | 1.387(4) |
| C(34)—C(35) | 1.382(4) |
| C(35)—C(36) | 1.377(4) |
| H(33)—O(33)—C(33) | 118(3) |
| H(6)—N(6)—C(7) | 104.9(15) |
| H(6)—N(6)—C(6) | 108.8(16) |
| C(7)—N(6)—C(6) | 110.7(2) |
| H(6)—N(6)—C(5) | 107.8(16) |
| C(7)—N(6)—C(5) | 114.5(2) |
| C(6)—N(6)—C(5) | 110.0(2) |
| C(1)—C(2)—C(3) | 112.7(3) |
| C(2)—C(3)—C(31) | 113.8(2) |
| C(2)—C(3)—C(4) | 110.8(2) |
| C(31)—C(3)—C(4) | 113.71(16) |
| C(5)—C(4)—C(41) | 111.75(18) |
| C(5)—C(4)—C(3) | 111.13(17) |
| C(41)—C(4)—C(3) | 112.08(19) |
| N(6)—C(5)—C(4) | 114.03(18) |
| C(32)—C(31)—C(36) | 118.5(2) |
| C(32)—C(31)—C(3) | 119.66(19) |
| C(36)—C(31)—C(3) | 121.8(2) |
| C(31)—C(32)—C(33) | 121.6(2) |
| O(33)—C(33)—C(34) | 117.5(2) |
| O(33)—C(33)—C(32) | 123.2(2) |
| C(34)—C(33)—C(32) | 119.3(2) |
| C(35)—C(34)—C(33) | 119.3(2) |
| C(36)—C(35)—C(34) | 121.2(2) |
| C(35)—C(36)—C(31) | 120.0(2) |

Symmetry transformations used to generate equivalent atoms:
Table 4d.
Hydrogen coordinates (× $10^4$) and isotropic
displacement parameters ($Å^2$ × $10^3$) for Form__B.

| | x | y | z | U(eq) |
|---|---|---|---|---|
| H(33) | 5160(4) | 660(2) | 3290(2) | 80(10) |
| H(6) | 4710(3) | 1983(17) | 7365(13) | 54(6) |
| H(1A) | 10962 | −753 | 5313 | 148 |
| H(1B) | 12620 | −460 | 5867 | 148 |
| H(1C) | 11980 | 419 | 5256 | 148 |
| H(2A) | 10815 | 871 | 6472 | 90 |
| H(2B) | 9682 | −266 | 6469 | 90 |
| H(3) | 9079 | 1455 | 5398 | 70 |
| H(4) | 8312 | 2119 | 6602 | 70 |
| H(5A) | 5415 | 492 | 6655 | 76 |
| H(5B) | 7293 | 388 | 7117 | 76 |
| H(6A) | 3594 | 393 | 7842 | 144 |
| H(6B) | 4128 | 1200 | 8512 | 144 |
| H(6C) | 5524 | 243 | 8264 | 144 |
| H(7A) | 7907 | 1923 | 8120 | 143 |
| H(7B) | 6200 | 2680 | 8366 | 143 |
| H(7C) | 7246 | 2922 | 7601 | 143 |
| H(32) | 6984 | 1181 | 4403 | 74 |
| H(34) | 4325 | −1772 | 4097 | 88 |
| H(35) | 5352 | −2351 | 5274 | 90 |
| H(36) | 7200 | −1195 | 6012 | 79 |

TABLE 4-continued

| H(41A) | 5030 | 2036 | 5700 | 120 |
|---|---|---|---|---|
| H(41B) | 6693 | 2879 | 5549 | 120 |
| H(41C) | 5506 | 2975 | 6295 | 120 |

Table 4e.
Anisotropic displacement parameters ($Å^2$ × $10^3$) for Form__B.
The anisotropic displacement factor exponent takes the form:
$-2 pi^2 [h^2 a^{*2} U11 + \ldots + 2 h k a^* b^* U12]$

| | U11 | U22 | U33 | U23 | U13 | U12 |
|---|---|---|---|---|---|---|
| Cl | 71(1) | 66(1) | 86(1) | 5(1) | −1(1) | −13(1) |
| O(33) | 102(1) | 107(1) | 74(1) | 12(1) | −17(1) | −43(1) |
| N(6) | 63(1) | 68(1) | 59(1) | 6(1) | 3(1) | 15(1) |
| C(1) | 68(1) | 106(2) | 122(3) | −12(2) | 14(2) | 17(2) |
| C(2) | 52(1) | 86(2) | 85(2) | −1(1) | −1(1) | 12(1) |
| C(3) | 52(1) | 64(1) | 60(1) | 5(1) | 4(1) | −2(1) |
| C(4) | 62(1) | 54(1) | 59(1) | 4(1) | −1(1) | 1(1) |
| C(5) | 68(1) | 58(1) | 65(1) | 5(1) | 9(1) | 9(1) |
| C(6) | 102(2) | 100(2) | 87(2) | 23(2) | 33(2) | 14(2) |
| C(7) | 95(2) | 118(2) | 73(2) | −21(2) | −12(2) | 0(2) |
| C(31) | 53(1) | 58(1) | 59(1) | 2(1) | 12(1) | 4(1) |
| C(32) | 60(1) | 63(1) | 61(1) | 0(1) | 8(1) | −8(1) |
| C(33) | 64(1) | 81(2) | 58(1) | −3(1) | 7(1) | −14(1) |
| C(34) | 69(1) | 71(1) | 81(2) | −11(1) | 15(1) | −16(1) |
| C(35) | 87(2) | 58(1) | 80(2) | 1(1) | 24(1) | −3(1) |
| C(36) | 72(1) | 58(1) | 67(1) | 4(1) | 13(1) | 6(1) |
| C(41) | 96(2) | 71(1) | 73(2) | 14(1) | 5(1) | 24(1) |

Example 14

RAMAN Spectrum of Forms A and B

Form A and B were investigated using RAMAN spectroscopy. The RAMAN spectrometer used was a Bruker Raman FT 100. The RAMAN Microscope was a Renishaw 1000 System, 20× Obj. Long working distance, diode laser 785 nm. Raman spectroscopy was able to distinguish clearly between Forms A and B. Differences between the spectra of the two forms appear in the whole spectral range (3200-50 $cm^{-1}$), but the difference in the range between 800-200 cm-1 were most significant.

The results for Form A are shown in FIG. 3, the results for Form B in FIG. 6.

Furthermore the samples were investigated by RAMAN microscopy. The spectra of both forms were also distinguishable. Here, spectra were taken in the wavenumber range of 2000-100 $cm^{-1}$.

Example 16

Variable Temperature X-Ray Powder Diffraction Experiment

A variable temperature X-ray powder diffraction experiment was run thereby producing Form B from Form A. Form A converted to Form B from 40-50° C. during the experiment. The result is reversible with Form B changing over into Form A at lower temperature.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:
1. A crystalline Form A of (−)-(1R,2R)-3-(3-dimethylamino-1-ethyl-2-methylpropyl)-phenol hydrochloride exhibiting at least X-ray lines (2-theta values) in a powder diffraction pattern when measured using Cu K$_\alpha$ radiation at 15.1±0.2, 16.0±0.2, 18.9±0.2, 20.4±0.2, 22.5±0.2, 27.3±0.2, 29.3±0.2 and 30.4±0.2.

2. The crystalline Form A of (−)-(1R,2R)-3-(3-dimethylamino-1-ethyl-2-methylpropyl)-phenol hydrochloride according to claim 1 exhibiting at least X-ray lines (2-theta values) in a powder diffraction when measured using Cu K$_\alpha$ radiation at 14.5±0.2, 18.2±0.2, 20.4±0.2, 21.7±0.2 and 25.5±0.2.

3. The crystalline Form A of (−)-(1R,2R)-3-(3-dimethylamino-1-ethyl-2-methylpropyl)-phenol hydrochloride according to claim 1 exhibiting an X-ray pattern (2-theta values) in a powder diffraction when measured using Cu K$_\alpha$ radiation essentially the same as that provided in FIG. 1.

4. The crystalline Form A of (−)-(1R,2R)-3-(3-dimethylamino-1-ethyl-2-methylpropyl)-phenol hydrochloride according to claim 1 wherein the crystal has a monoclinic form.

5. A process for producing a (−)-(1R,2R)-3-(3-dimethylamino-1-ethyl-2-methylpropyl)-phenol hydrochloride of crystalline Form A, said process comprising:
dissolving a (−)-(1R,2R)-3-(3-dimethylamino-1-ethyl-2-methylpropyl)-phenol hydrochloride of crystalline Form B in acetone, acetonitrile or isopropanol to form a solution:
leaving the solution to crystallize and
isolating crystals of (−)-(1R,2R)-3-(3-dimethylamino-1-ethyl-2-methylpropyl)-phenol hydrochloride of crystalline Form A;
wherein during the process the temperature is kept below +40° C.

6. The process for producing a (−)-(1R,2R)-3-(3-dimethylamino-1-ethyl-2-methylpropyl)-phenol hydrochloride of crystalline Form A according to claim 5 wherein during the process the temperature is kept below +25° C.

7. The process of claim 5 wherein said (−)-(1R,2R)-3-(3-dimethylamino-1-ethyl-2-methylpropyl)-phenol hydrochloride of Form B is dissolved in acetonitrile, and further comprising the steps of:
stirring the solution;
removing insoluble residue by filtering and
evaporating the acetonitrile leaving (−)-(1R,2R)-3-(3-dimethylamino-1-ethyl-2-methylpropyl)-phenol hydrochloride of Form A to crystallize.

8. The process according to claim 5 wherein said (−)-(1R,2R)-3-(3-dimethylamino-1-ethyl-2-methylpropyl)-phenol hydrochloride of crystalline Form B is dissolved in isopropanol at temperatures above room temperature, and after complete dissolution no further heat is provided and further comprising:
adding seed crystals of (−)-(1R,2R)-3-(3-dimethylamino-1-ethyl-2-methylpropyl)-phenol hydrochloride of crystalline Form A and then cooling the mixture down to ≦15° C.

9. The process of claim 8, wherein said (−)-(1R,2R)-3-(3-dimethyl-amino-1-ethyl-2-methylpropyl)-phenol hydrochloride of crystalline Form B is dissolved in isopropanol at a temperature above 65° C. but not exceeding 80° C.

10. The process of claim 8, wherein said mixture is cooled down to ≦10° C.

11. The process of claim 8, wherein said mixture is cooled down to ≦5° C.

12. The process according to claim 5 further comprising redissolving the (−)-(1R,2R)-3-(3-dimethylamino-1-ethyl-2-methylpropyl)-phenol hydrochloride of crystalline Form A in a solvent selected from acetone, acetonitrile and isopropanol, then optionally filtering the solution to remove any insoluble residue and optionally reducing the amount of solvent by evaporation, then allowing the solution to crystallize.

13. The process of claim 12, wherein said solvent is the same as that used to form the (−)-(1R,2R)-3-(3-dimethylamino-1-ethyl-2-methylpropyl)-phenol hydrochloride of crystalline Form A before the step of redissovling.

14. The process of claim 12, wherein during the step of allowing the solution to crystallize, the temperature is maintained at ≦15° C.

15. The process of claim 12, wherein during the step of allowing the solution to crystallize, the temperature is maintained at ≦10° C.

16. The process of claim 12, wherein during the step of allowing the solution to crystallize, the temperature is maintained at ≦5° C.

17. A process for producing crystalline Form A of (−)-(1R,2R)-3-(3-dimethylamino-1-ethyl-2-methylpropyl)-phenol hydrochloride comprising the step of cooling (−)-(1R,2R)-3-(3-dimethylamino-1-ethyl-2-methylpropyl)-hydrochloride phenol of Form B for a time between 24 hours and 168 hours at a temperature of between −4° C. and −80° C.

18. The process of claim 17 wherein the cooling temperature is between −10° C. and −60° C.

19. The process of claim 17, wherein the cooling temperature is between −15° C. and −50° C.

20. The process of claim 17, wherein the cooling temperature is between −25° C. and −40° C.

21. The process of claim 17, wherein the cooling is carried out for a time between 24 hours and 120 hours.

22. The process of claim 17, wherein the cooling is carried out for a time between 24 hours and 72 hours.

23. The process of claim 17, wherein the cooling is carried out for a time between 24 hours and 48 hours.

24. A crystalline Form A of (−)-(1R,2R)-3-(3-dimethylamino-1-ethyl-2-methylpropyl)-phenol hydrochloride according to claim 1, produced by the process of:
dissolving (−) (−)-(1R,2R)-3-(3-dimethylamino-1-ethyl-2-methylpropyl)-phenol hydrochloride of Form B in acetonitrile together with active carbon,
heating the solution to the boiling point,
removing the active carbon by filtering,
stirring the solution at a temperature below 40° C.,
removing insoluble residue by filtering and removing part of the solvent,
leaving (−)-(1R,2R)-3-(3-dimethylamino-1-ethyl-2-methylpropyl)-phenol hydrochloride of Form A to crystallize,
redissolving the resulting crystals in acetonitrile,
removing insoluble residue by filtering and removing part of the solvent, and
leaving (−)-(1R,2R)-3-(3-dimethylamino-1-ethyl-2-methylpropyl)-phenol hydrochloride of Form A to crystallize.

25. A solid pharmaceutical composition comprising, as an active ingredient, a crystalline Form A of (−)-(1R,2R)-3-(3-dimethylamino-1-ethyl-2-methylpropyl)-phenol hydrochloride exhibiting at least X-ray lines (2-theta values) in a powder diffraction pattern when measured using Cu K$_\alpha$ radiation at 15.1±0.2, 16.0±0.2, 18.9±0.2, 20.4±0.2, 22.5±0.2, 27.3±0.2, 29.3±0.2 and 30.4±0.2, and at least one suitable additive or auxiliary substance.

26. A solid pharmaceutical composition comprising, as an active ingredient, a crystalline Form A of (−)-(1R,2R)-3-(3-dimethylamino-1-ethyl-2-methylpropyl)-phenol hydrochloride according to claim 25, produced by the process of:

dissolving (−)-(1R,2R)-3-(3-dimethylamino-1-ethyl-2-methylpropyl)-phenol hydrochloride of Form B in acetonitrile together with active carbon,
heating the solution to the boiling point,
removing the active carbon by filtering,
stirring the solution at a temperature below 40° C.,
removing insoluble residue by filtering and removing part of the solvent,
leaving (−)-(1R,2R)-3-(3-dimethylamino-1-ethyl-2-methylpropyl)-phenol hydrochloride of Form A to crystallize, and
redissolving the resulting crystals in acetonitrile,
removing insoluble residue by filtering and removing part of the solvent, and
leaving (−)-(1R,2R)-3-(3-dimethylamino-1-ethyl-2-methylpropyl)-phenol hydrochloride of Form A to crystallize, and
at least one suitable additive or auxiliary substance.

27. A method of treating or inhibiting pain or urinary incontinence, said method comprising the step of administering a pharmaceutically effective amount of a crystalline Form A of (−)-(1R,2R)-3-(3-dimethylamino-1-ethyl-2-methylpropyl)-phenol hydrochloride exhibiting at least X-ray lines (2-theta values) in a powder diffraction pattern when measured using Cu K$_\alpha$ radiation at 15.1±0.2, 16.0±0.2, 18.9±0.2, 20.4±0.2, 22.5±0.2, 27.3±0.2, 29.3±0.2 and 30.4±0.2 to a subject in need thereof.

* * * * *